US011318119B2

(12) United States Patent
Cho et al.

(10) Patent No.: US 11,318,119 B2
(45) Date of Patent: May 3, 2022

(54) HIV PROTEASE INHIBITORS

(71) Applicant: Gilead Sciences, Inc., Foster City, CA (US)

(72) Inventors: Aesop Cho, Mountain View, CA (US); John O. Link, San Francisco, CA (US); Jie Xu, Foster City, CA (US)

(73) Assignee: Gilead Sciences, Inc., Foster City, CA (US)

(*) Notice: Subject to any disclaimer, the term of this patent is extended or adjusted under 35 U.S.C. 154(b) by 77 days.

(21) Appl. No.: 16/849,747

(22) Filed: Apr. 15, 2020

(65) Prior Publication Data
US 2020/0345699 A1 Nov. 5, 2020

Related U.S. Application Data

(60) Provisional application No. 62/835,244, filed on Apr. 17, 2019.

(51) Int. Cl.
| | |
|---|---|
| *A61K 31/4196* | (2006.01) |
| *A61K 31/52* | (2006.01) |
| *A61K 31/537* | (2006.01) |
| *A61K 31/675* | (2006.01) |
| *A61K 45/06* | (2006.01) |
| *A61P 31/18* | (2006.01) |
| *A61K 31/7076* | (2006.01) |
| *C07D 403/10* | (2006.01) |
| *C07D 403/14* | (2006.01) |

(52) U.S. Cl.
CPC .......... *A61K 31/4196* (2013.01); *A61K 31/52* (2013.01); *A61K 31/537* (2013.01); *A61K 31/675* (2013.01); *A61K 31/7076* (2013.01); *A61K 45/06* (2013.01); *A61P 31/18* (2018.01); *C07D 403/10* (2013.01); *C07D 403/14* (2013.01)

(58) Field of Classification Search
CPC .. A61K 31/4196; A61K 31/52; A61K 31/537; A61K 31/675; A61K 31/7076; A61K 45/06; A61P 31/18; C07D 403/10; C07D 403/14
USPC .......................................................... 514/46
See application file for complete search history.

(56) References Cited

U.S. PATENT DOCUMENTS

| | | | |
|---|---|---|---|
| 5,243,054 | A | 9/1993 | Naka et al. |
| 10,774,053 | B2 * | 9/2020 | Cai ..................... C07D 405/14 |
| 2006/0040999 | A1 | 2/2006 | Ali et al. |
| 2007/0155750 | A1 | 7/2007 | Neamati et al. |
| 2009/0186926 | A1 | 7/2009 | Sheth et al. |
| 2011/0065916 | A1 | 3/2011 | Spyvee et al. |
| 2014/0179751 | A1 | 6/2014 | Graef et al. |
| 2015/0376136 | A1 | 12/2015 | Chumakova et al. |
| 2016/0024071 | A1 | 1/2016 | Garofalo et al. |

FOREIGN PATENT DOCUMENTS

| | | |
|---|---|---|
| TW | I360542 B | 3/2012 |
| WO | WO-2005/058311 A1 | 6/2005 |
| WO | WO-2007/079186 A2 | 7/2007 |
| WO | WO-2007/081569 A2 | 7/2007 |
| WO | WO-2007/081571 A2 | 7/2007 |
| WO | WO-2007/092642 A2 | 8/2007 |
| WO | WO-2008103351 A2 | 8/2008 |
| WO | WO-2011/133719 A2 | 10/2011 |
| WO | WO-2014/145331 A1 | 9/2014 |
| WO | WO-2017/142821 A1 | 8/2017 |
| WO | WO-2018/106519 A1 | 6/2018 |
| WO | WO-2018/118829 A1 | 6/2018 |
| WO | WO 2019075291 * | 4/2019 |

OTHER PUBLICATIONS

Glossary of medical education terms, Institute of International Medical Education. http://www.iime.org/glossary.htm Accessed in Mar. 2013. (Year: 2013).*
International Search Report and Written Opinion dated Jan. 3, 2019 on International Application No. PCT/US2018/055554.
Office Action dated Oct. 7, 2019 for Taiwan Appl. No. 107128405.
Office Action dated Jan. 2, 2020 for Gulf Cooperation Council Appl. No. 2018-36190.
Third Party Observation dated Feb. 14, 2020 for International Appl. No. PCT/US2018/055554.
Ali, A., et al., Discovery of HIV-1 Protease Inhibitors with Picomolar Affinities Incorporating N-Aryl-oxazolidinone-5-carboxamides as Novel P2 Ligands, Journal of Medicinal Chemistry, 2006, 49:7342-7356.
International Search Report and Written Opinion dated Jul. 10, 2020 on International Application No. PCT/US2020/028336.

* cited by examiner

*Primary Examiner* — Yih-Horng Shiao

(57) ABSTRACT

The present disclosure provides compounds, or a pharmaceutically acceptable salt thereof as described herein, useful for treating the proliferation of the HIV virus, treating AIDS or delaying the onset of AIDS symptoms in a subject. The disclosure also provides pharmaceutical compositions comprising these compounds, processes for preparing them, therapeutic methods for treating the proliferation of the HIV virus, treating AIDS or delaying the onset of AIDS symptoms in a subject using these compounds. The present disclosure also provides compounds, or a pharmaceutically acceptable salt thereof as described herein, useful for treating the proliferation of a coronavirus, treating coronavirus symptoms or delaying the onset of coronavirus symptoms in a subject. The disclosure also provides pharmaceutical compositions comprising these compounds, processes for preparing them, therapeutic methods for treating the proliferation of a coronavirus, treating coronavirus symptoms or delaying the onset of coronavirus symptoms in a subject using these compounds.

18 Claims, No Drawings
Specification includes a Sequence Listing.

HIV PROTEASE INHIBITORS

CROSS-REFERENCES TO RELATED APPLICATIONS

This patent application claims the benefit under 35 U.S.C. § 119(e) of U.S. Provisional Patent Application No. 62/835,244, filed Apr. 17, 2019. The foregoing application is incorporated herein by reference in its entirety.

FIELD

The present disclosure relates to compounds for use in the treatment of Retroviridae viral infection including infections caused by the HIV virus. The present disclosure also relates to compounds for use in the treatment of Coronaviridae virus infections, including infections caused by the SARS virus, the MERS virus, or the 2019-nCoV (COVID-19) virus. The present disclosure also relates to preparation of the compounds provided herein and their intermediates, and pharmaceutical compositions comprising compounds provided herein.

BACKGROUND

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Several protease inhibitors (PI) are presently approved for use in AIDS or HIV. Yet many PI inhibitors suffer from high rates of hepatic metabolism, which may require co-administration of a booster or more frequent dosing. Furthermore, viral resistance remains a problem. Accordingly, there is a need for new compounds that inhibit the replication of HIV.

Human coronaviruses, first identified in the mid-1960s, are common viruses that infect most people at some time in their life, generally causing mild to moderate upper respiratory and gastrointestinal tract illnesses. The coronavirus referred to as "Middle East Respiratory Syndrome Coronavirus" (MERS-CoV or MERS) was first reported in Saudi Arabia in 2012 and has spread to several other countries. SARS-CoV, the coronavirus responsible for Severe Acute Respiratory Syndrome (SARS) was first recognized in China in 2002 and led to a worldwide outbreak in 2002 and 2003. Recently, a novel coronavirus has been identified in the City of Wuhan, China (Wuhan coronavirus; 2019-nCoV). Currently, an outbreak of 2019-nCoV associated pneumonia is taking place in China. There is a need for new compounds that inhibit the replication of 2019-nCoV (COVID-19).

SUMMARY

The present disclosure provides compounds and methods for the treatment of an HIV infection. The present disclosure also provides compounds and methods for the treatment of a coronavirus infection, including an infection caused by the SARS virus, the MERS virus, or the 2019-nCoV (COVID-19) virus. Provided herein are compounds selected from:

| Compound # | Structure |
|---|---|
| 1 | 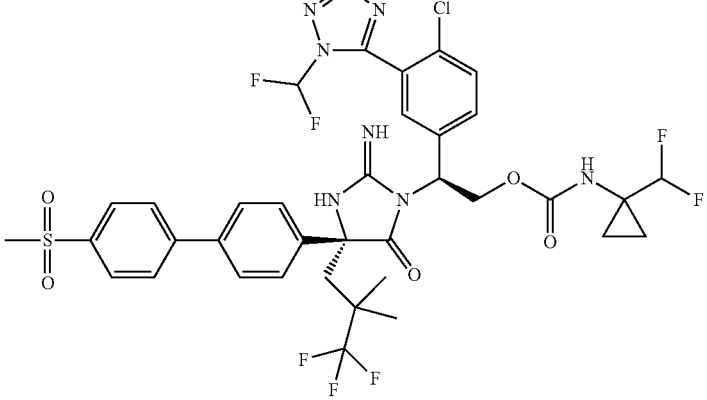 |
| 2 | 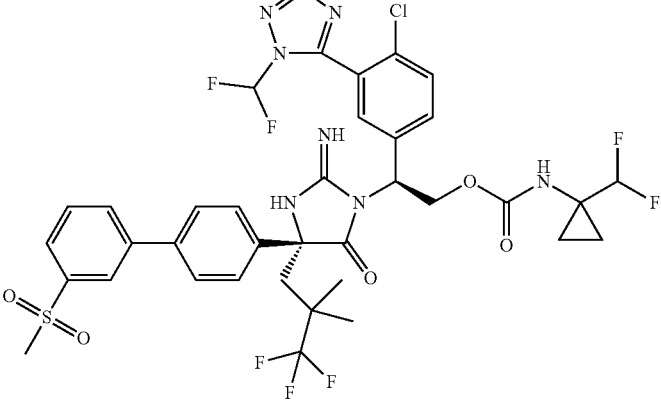 |

-continued
| Compound # | Structure |
|---|---|
| 3 | 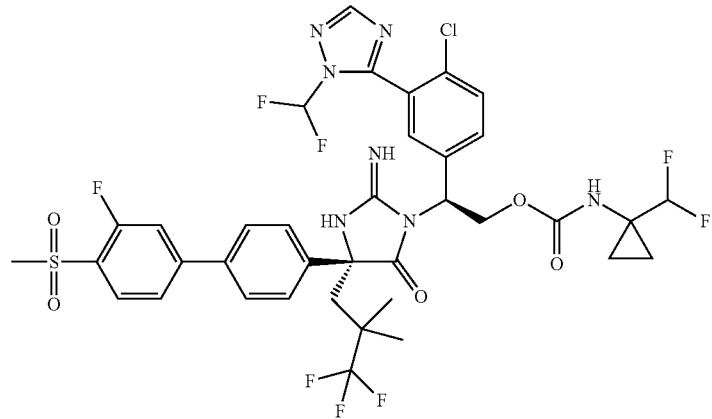 |
| 4 | 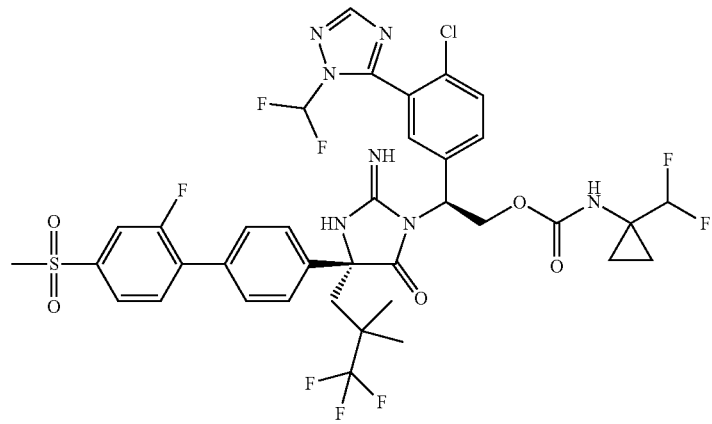 [SMILES: CC(C)(C[C@]1(c2ccc(-c3ccc(S(C)(=O)=O)cc3F)cc2)NC(=N)N([C@H](COC(=O)NC2(C(F)F)CC2)c2ccc(Cl)c(-c3ncnn3C(F)F)c2)C1=O)C(F)(F)F] |
| 5 | 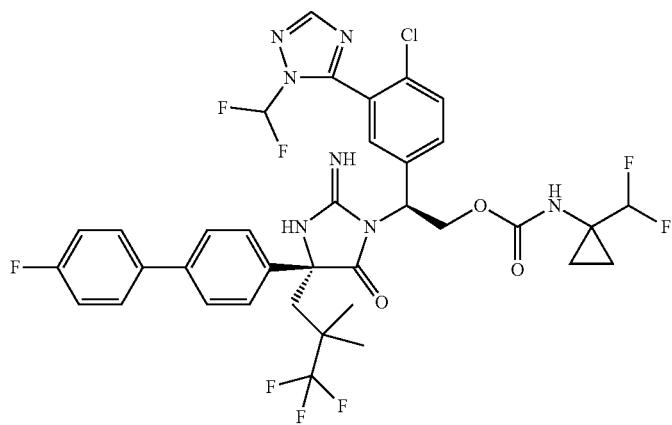 [SMILES: CC(C)(C[C@]1(c2ccc(-c3ccc(F)cc3)cc2)NC(=N)N([C@H](COC(=O)NC2(C(F)F)CC2)c2ccc(Cl)c(-c3ncnn3C(F)F)c2)C1=O)C(F)(F)F] |

-continued
| Compound # | Structure |
|---|---|
| 6 | 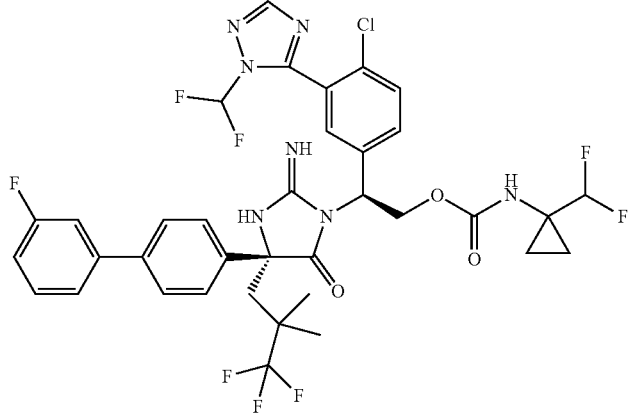 [SMILES: CC(C)(C[C@]1(c2ccc(-c3cccc(F)c3)cc2)NC(=N)N([C@H](COC(=O)NC2(C(F)F)CC2)c2ccc(Cl)c(-c3ncnn3C(F)F)c2)C1=O)C(F)(F)F] |
| 7 | 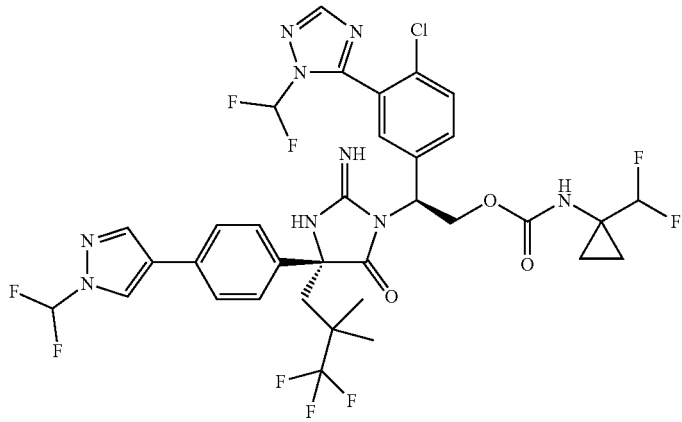 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] |
| 8 | 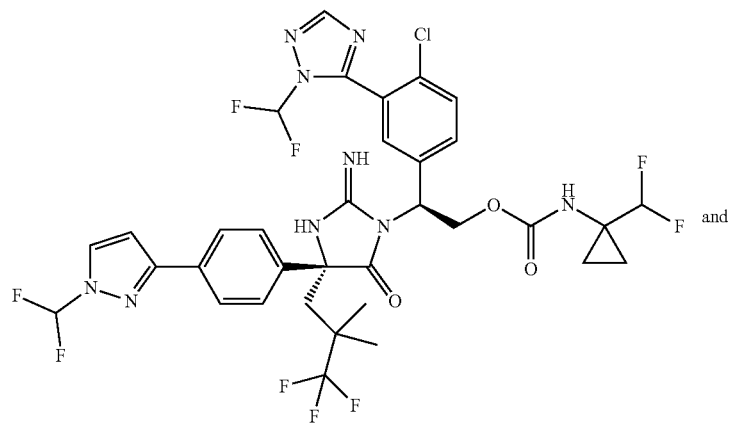 [SMILES: CC(C)(C[C@]1(c2ccc(-c3ccn(C(F)F)n3)cc2)NC(=N)N([C@H](COC(=O)NC2(C(F)F)CC2)c2ccc(Cl)c(-c3ncnn3C(F)F)c2)C1=O)C(F)(F)F] and |

| Compound # | Structure |
|---|---|
| 9 | 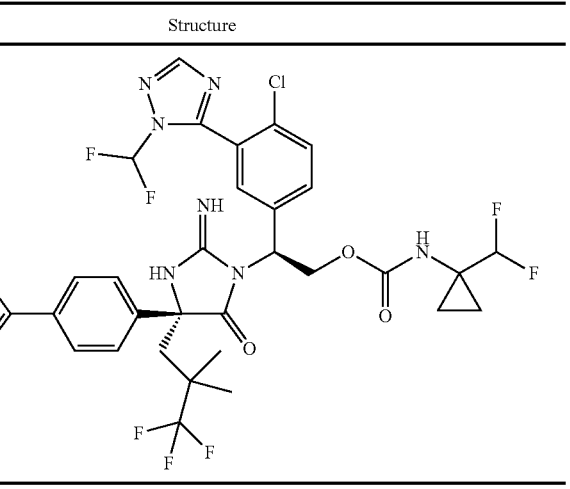 | or a pharmaceutically acceptable salt thereof.

Also provided are pharmaceutical compositions comprising a therapeutically effective amount of a compound disclosed herein, or a pharmaceutically acceptable salt thereof, and a pharmaceutically acceptable excipient. In certain embodiments, the pharmaceutical composition further comprises one or more additional therapeutic agents.

Also provided is a method of treating or preventing human immunodeficiency virus (HIV) infection comprising administering a therapeutically effective amount of a compound disclosed herein, or a pharmaceutically acceptable salt thereof, to a subject in need thereof.

Also provided is a method of treating or preventing coronavirus infection comprising administering a therapeutically effective amount of a compound disclosed herein, or a pharmaceutically acceptable salt thereof, to a subject in need thereof. In certain embodiments, the coronavirus infection is an infection caused by the SARS virus, the MERS virus, or the 2019-nCoV (COVID-19) virus.

DETAILED DESCRIPTION

The following is a list of abbreviations and acronyms used throughout the application:

| Abbreviation | Meaning |
|---|---|
| ° C. | Degree Celsius |
| ATP | Adenosine-5'-triphosphate |
| aq | Aqueous |
| calc'd | Calculated |
| compd | Compound |
| d | Doublet |
| dd | Doublet of doublets |
| DCM | Dichloromethane |
| DIPEA | N,N-diisopropylethylamine |
| DMSO | Dimethylsulfoxide |
| EtOAc | Ethyl acetate |
| equiv/eq | Equivalents |
| ESI | Electrospray ionization |
| Ac | Acetate |
| Et | Ethyl |
| g | Grams |
| HPLC | High-performance liquid chromatography |
| h/hr | Hours |
| Hz | Hertz |
| IC$_{50}$ | The half maximal inhibitory concentration |
| J | Coupling constant |
| Kg | Kilogram |
| M | Molar |
| m | Multiplet |
| m/z | mass-to-charge ratio |
| M+ | Mass peak |
| M + H | Mass peak plus hydrogen |
| Me | Methyl |
| MeOH | Methyl alcohol/methanol |
| mg | Milligram |
| MHz | Megahertz |
| min/m | Minute |
| ml/mL | Milliliter |
| mM | Millimolar |
| mmol | Millimole |
| MS | Mass spectroscopy |
| mw | Microwave |
| N | Normal |
| mol | Mole |
| nM | Nanomolar |
| nmol | Nanomole |
| NMR | Nuclear magnetic resonance |
| Ph | Phenyl |
| ppm | Parts per million |
| prep | Preparative |
| Rf | Retention factor |
| RP | Reverse phase |
| RT/rt | Room temperature |
| s | Second |
| s | Singlet |
| t | Triplet |
| TEA | Triethylamine |
| TFA | Trifluoroacetic acid |
| TMS | trimethylsilyl |
| δ | Chemical shift |
| μg | Microgram |
| μL/μl | Microliter |
| μM | Micromolar |
| μm | Micrometer |
| μmol | Micromole |

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

"A compound disclosed herein" or "a compound of the present disclosure" refers to the compounds of Examples 1-9 (Compounds 1-9).

The compounds described herein include isomers, stereoisomers and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound of the present disclosure and includes geometric isomers. It is understood that a substituent may be attached at a chiral center of a carbon atom. Therefore, the disclosure includes enantiomers, diastereomers or racemates of the compound.

"Enantiomers" are a pair of stereoisomers that are non-superimposable mirror images of each other. A 1:1 mixture of a pair of enantiomers is a "racemic" mixture.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, including racemic and scalemic mixtures, optically pure forms and intermediate mixtures. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"$IC_{95}$" or "$EC_{95}$" refers to the inhibitory concentration required to achieve 95% of the maximum desired effect, which in many cases here is the inhibition of the HIV virus. This term is obtained using an in vitro assay evaluating the concentration-dependent inhibition of wild type HIV virus.

"$IC_{50}$" or "$EC_{50}$" refers to the inhibitory concentration required to achieve 50% of the maximum desired effect, which in many cases here is the inhibition of the HIV virus. This term is obtained using an in vitro assay evaluating the concentration-dependent inhibition of wild type HIV virus.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

The present disclosure also provides for prodrugs of the compounds disclosed herein. A "prodrug" is defined in the pharmaceutical field as a biologically inactive derivative of a drug that upon administration to the human body is converted to the biologically active parent drug according to some chemical or enzymatic pathway.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS or of COVID-19 related symptoms is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's $HIV^+$ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Moreover, the term "preventing coronavirus infection" refers to administering to a subject who does not have a detectable coronavirus infection (e.g., a MERS, SARS, or COVID-19 infection) an anti-coronavirus therapeutic substance. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

The compounds described herein include solvates, hydrates, tautomers, stereoisomers and salt forms thereof.

Provided are also compounds in which from 1 to n specified or unspecified hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorus, fluorine, chlorine, and iodine such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of provided herein, can generally be prepared by conventional techniques known to those skilled in the art or by processes analogous to those described in the Examples as set out below using an appropriate isotopically-labeled reagent in place of the non-labeled reagent previously employed.

Additionally, the compounds described herein may be covalently bound to a polyethylene glycol (PEG) substituent, i.e. "pegylated" in order to enhance pharmacokinetic and metabolic profiles.

As referenced herein, darunavir is a HIV protease inhibitor having the structure:

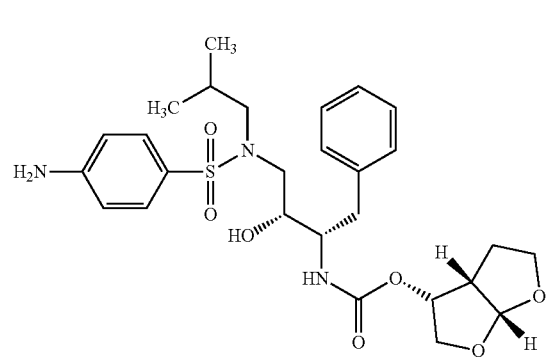

and having the IUPAC name [(3aS,4R,6aR)-2,3,3a,4,5,6a-hexahydrofuro[2,3-b]furan-4-yl] N-[(2 S,3R)-4-[(4-aminophenyl)sulfonyl-(2-methylpropyl)amino]-3-hydroxy-1-phenylbutan-2-yl]carbamate. Darunavir (DRV) is marketed under the brand name PREZISTA®.

As referenced herein, atazanavir is a HIV protease inhibitor having the structure:

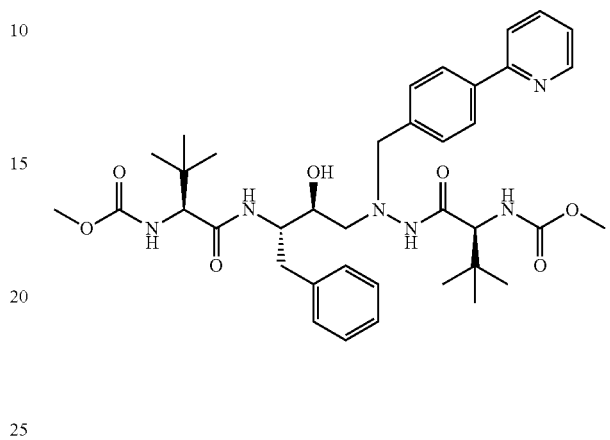

and having the IUPAC name methyl N-[(2S)-1-[2-[(2S,3S)-2-hydroxy-3-[[(2S)-2-(methoxycarbonylamino)-3,3-dimethylbutanoyl]amino]-4-phenylbutyl]-2-[(4-pyridin-2-ylphenyl)methyl]hydrazinyl]-3,3-dimethyl-1-oxobutan-2-yl]carbamate. Atazanavir (ATV) is marketed under the brand name REYATAZ®.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Provided herein are compounds selected from:

| Compound # | Structure |
|---|---|
| 1 | 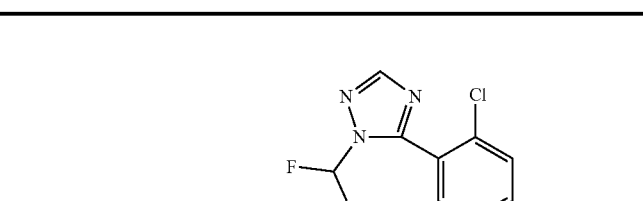 |

-continued
| Compound # | Structure |
|---|---|
| 2 | 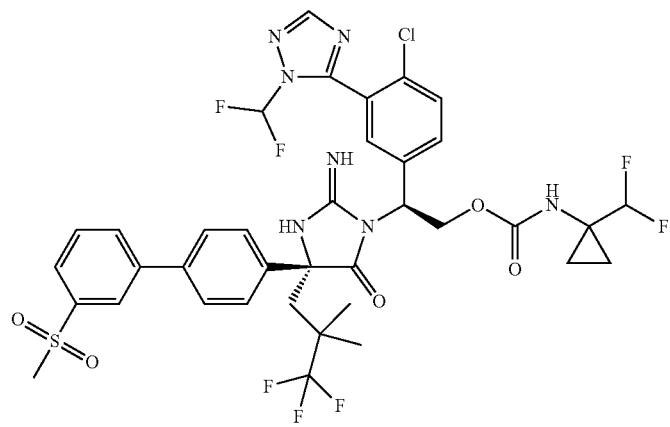 [SMILES: CC(C)(C[C@]1(c2ccc(-c3cccc(S(C)(=O)=O)c3)cc2)NC(=N)N([C@H](COC(=O)NC2(C(F)F)CC2)c2ccc(Cl)c(-c3ncnn3C(F)F)c2)C1=O)C(F)(F)F] |
| 3 | 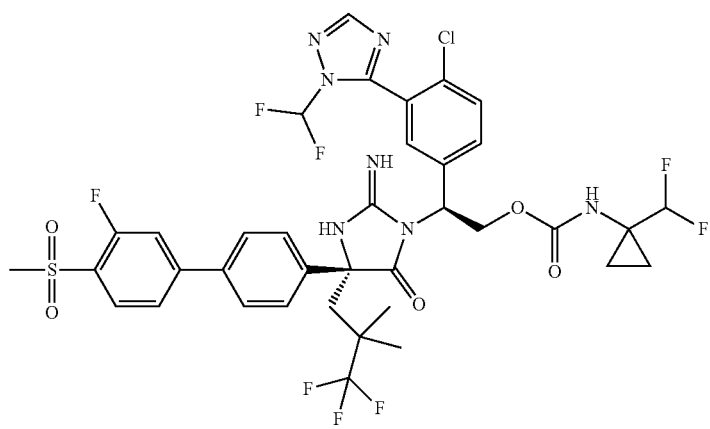 |
| 4 | 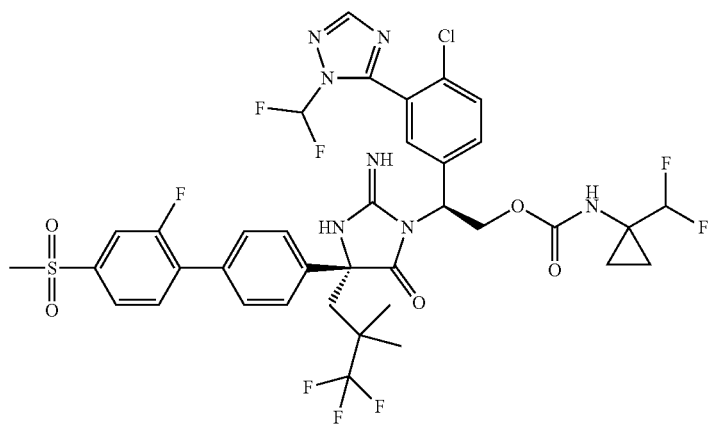 [SMILES: CC(C)(C[C@]1(c2ccc(-c3ccc(S(C)(=O)=O)cc3F)cc2)NC(=N)N([C@H](COC(=O)NC2(C(F)F)CC2)c2ccc(Cl)c(-c3ncnn3C(F)F)c2)C1=O)C(F)(F)F] |

-continued
| Compound # | Structure |
|---|---|
| 5 | 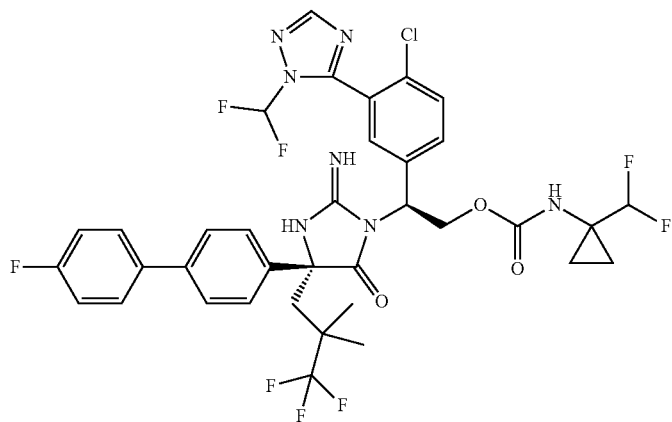 [SMILES: CC(C)(C[C@]1(c2ccc(-c3ccc(F)cc3)cc2)NC(=N)N([C@H](COC(=O)NC2(C(F)F)CC2)c2ccc(Cl)c(-c3ncnn3C(F)F)c2)C1=O)C(F)(F)F] |
| 6 | 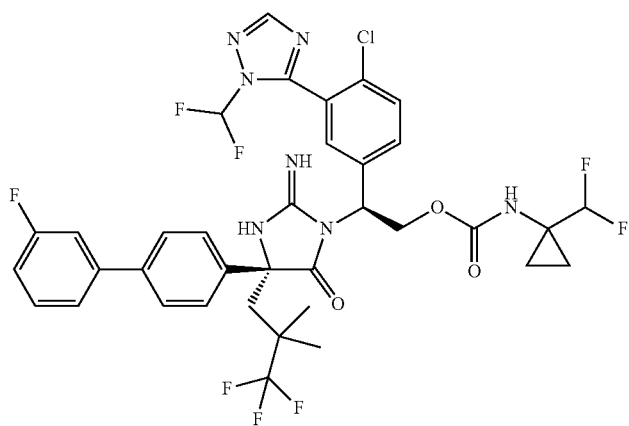 [SMILES: CC(C)(C[C@]1(c2ccc(-c3cccc(F)c3)cc2)NC(=N)N([C@H](COC(=O)NC2(C(F)F)CC2)c2ccc(Cl)c(-c3ncnn3C(F)F)c2)C1=O)C(F)(F)F] |
| 7 | 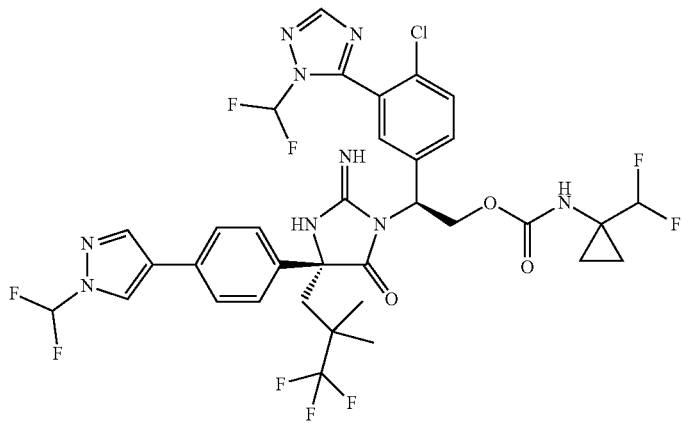 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] |

-continued
| Compound # | Structure |
|---|---|
| 8 | 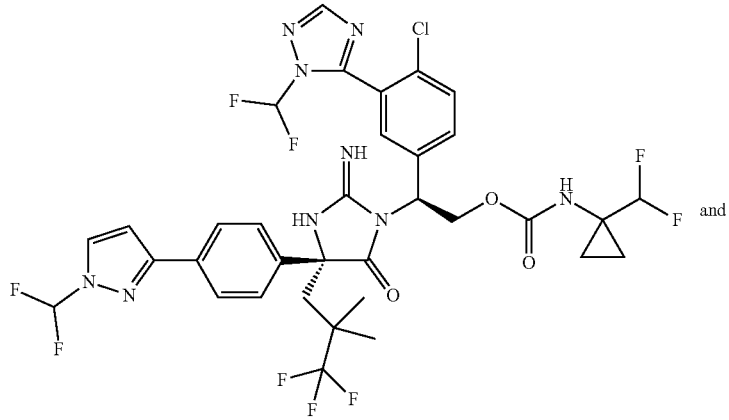 [SMILES: CC(C)(C[C@]1(c2ccc(-c3ccn(C(F)F)n3)cc2)NC(=N)N([C@H](COC(=O)NC2(C(F)F)CC2)c2ccc(Cl)c(-c3ncnn3C(F)F)c2)C1=O)C(F)(F)F] and |
| 9 | 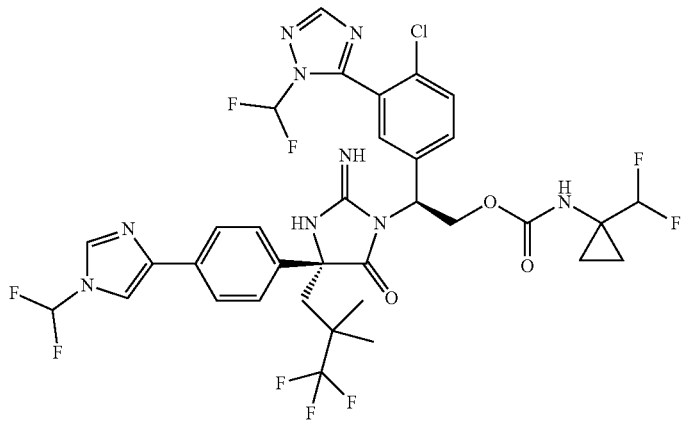 [SMILES: CC(C)(C[C@]1(c2ccc(-c3cn(C(F)F)cn3)cc2)NC(=N)N([C@H](COC(=O)NC2(C(F)F)CC2)c2ccc(Cl)c(-c3ncnn3C(F)F)c2)C1=O)C(F)(F)F] |
or a pharmaceutically acceptable salt thereof.
Provided herein are compounds selected from:
| Compound # | Structure |
|---|---|
| 1 | 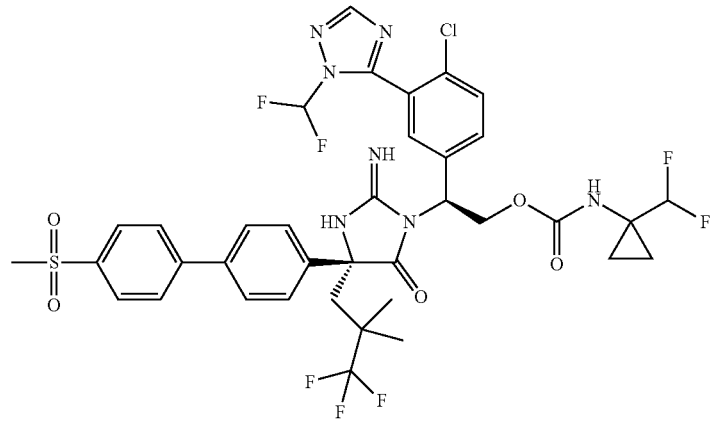 [SMILES: CC(C)(C[C@]1(c2ccc(-c3ccc(S(C)(=O)=O)cc3)cc2)NC(=N)N([C@H](COC(=O)NC2(C(F)F)CC2)c2ccc(Cl)c(-c3ncnn3C(F)F)c2)C1=O)C(F)(F)F] |

-continued
| Compound # | Structure |
|---|---|
| 2 | 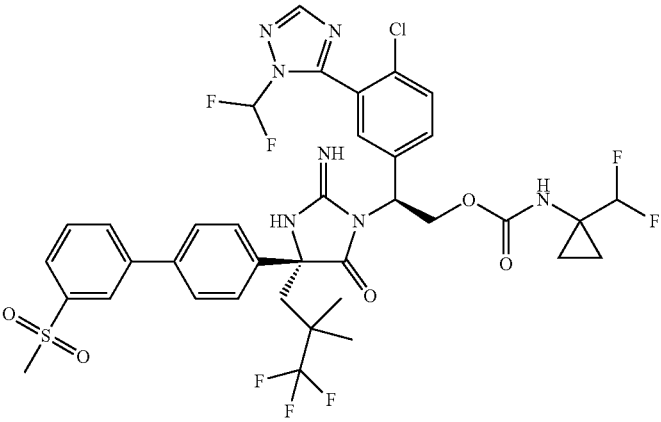 [SMILES: CC(C)(C[C@]1(c2ccc(-c3cccc(S(C)(=O)=O)c3)cc2)NC(=N)N([C@H](COC(=O)NC2(C(F)F)CC2)c2ccc(Cl)c(-c3ncnn3C(F)F)c2)C1=O)C(F)(F)F] |
| 3 | 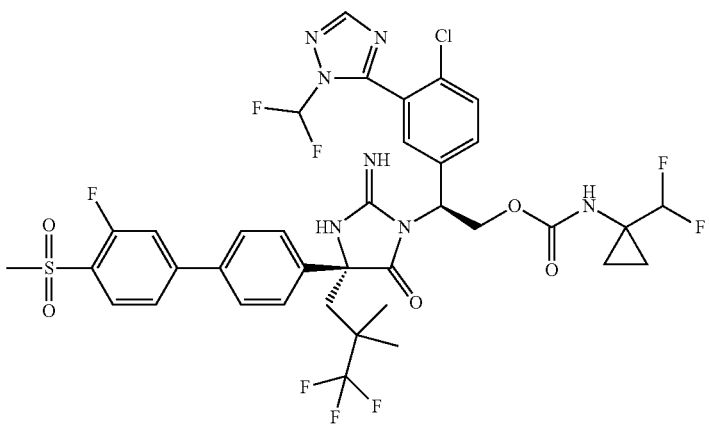 |
| 4 | 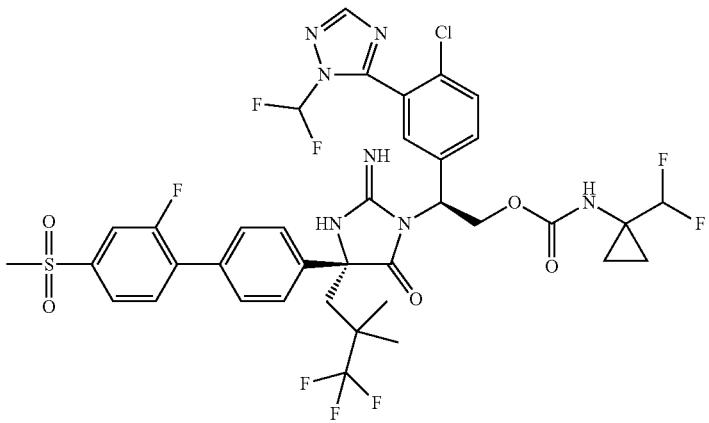 [SMILES: CC(C)(C[C@]1(c2ccc(-c3ccc(S(C)(=O)=O)cc3F)cc2)NC(=N)N([C@H](COC(=O)NC2(C(F)F)CC2)c2ccc(Cl)c(-c3ncnn3C(F)F)c2)C1=O)C(F)(F)F] |

-continued

| Compound # | Structure |
|---|---|
| 7 | 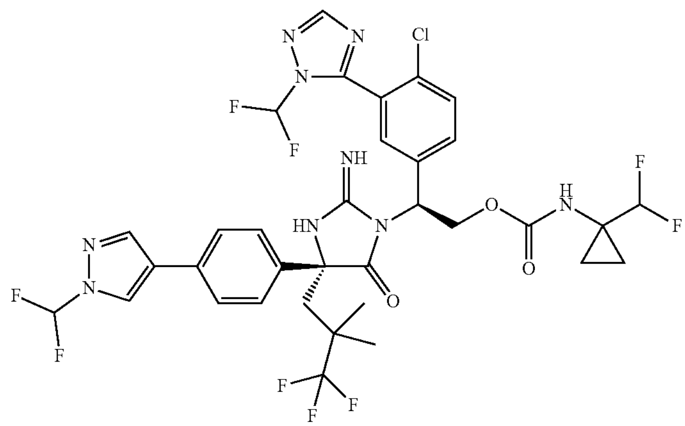 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] |
| 8 | 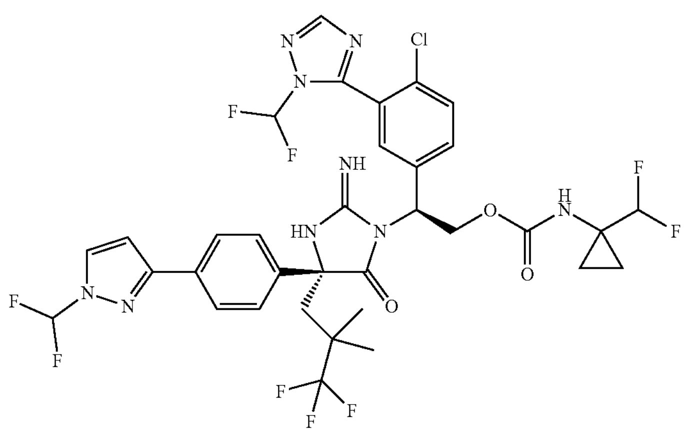 |
| 9 | | or a pharmaceutically acceptable salt thereof.

Provided herein are compounds selected from:
| Compound # | Structure |
|---|---|
| 1 | 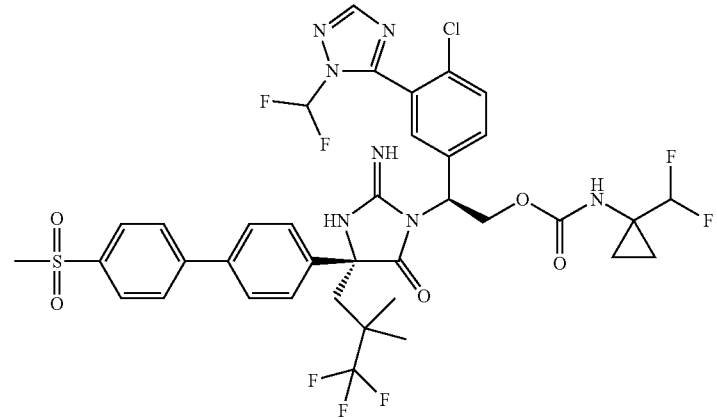 [SMILES: CC(C)(C[C@]1(c2ccc(-c3ccc(S(C)(=O)=O)cc3)cc2)NC(=N)N([C@H](COC(=O)NC2(C(F)F)CC2)c2ccc(Cl)c(-c3ncnn3C(F)F)c2)C1=O)C(F)(F)F] |
| 3 | 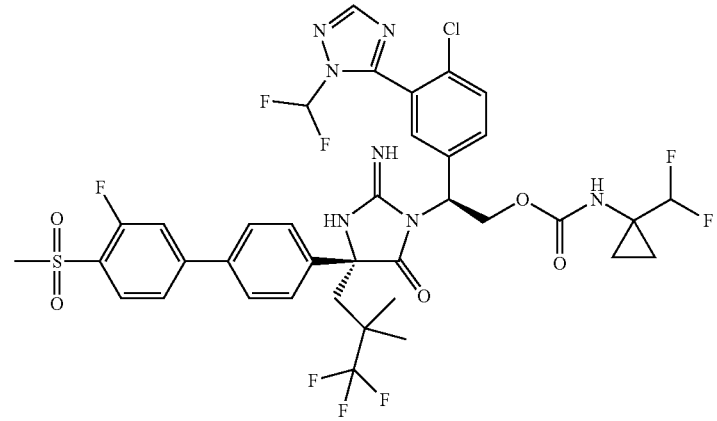 [SMILES: CC(C)(C[C@]1(c2ccc(-c3ccc(S(C)(=O)=O)c(F)c3)cc2)NC(=N)N([C@H](COC(=O)NC2(C(F)F)CC2)c2ccc(Cl)c(-c3ncnn3C(F)F)c2)C1=O)C(F)(F)F] |
| 4 | 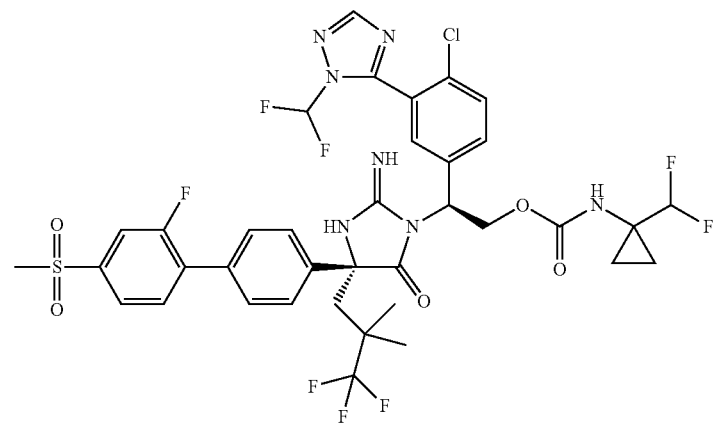 [SMILES: CC(C)(C[C@]1(c2ccc(-c3ccc(S(C)(=O)=O)cc3F)cc2)NC(=N)N([C@H](COC(=O)NC2(C(F)F)CC2)c2ccc(Cl)c(-c3ncnn3C(F)F)c2)C1=O)C(F)(F)F] |

| Compound # | Structure |
|---|---|
| 7 | 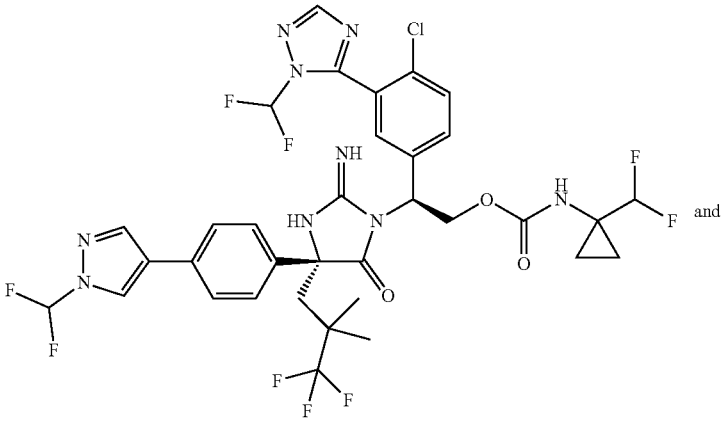 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] and |
| 8 | 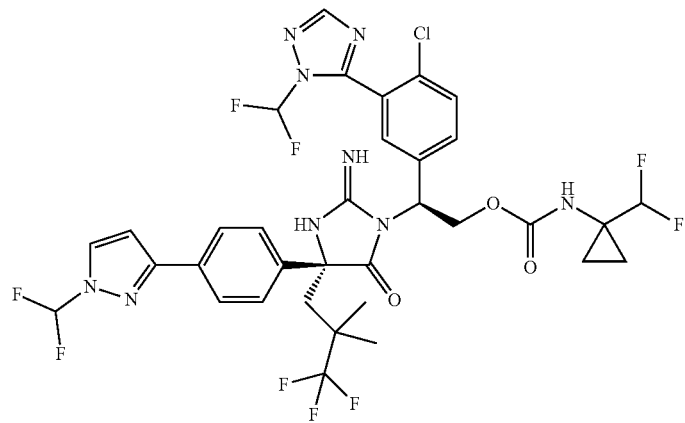 [SMILES: CC(C)(C[C@]1(c2ccc(-c3ccn(C(F)F)n3)cc2)NC(=N)N([C@H](COC(=O)NC2(C(F)F)CC2)c2ccc(Cl)c(-c3ncnn3C(F)F)c2)C1=O)C(F)(F)F] |
or a pharmaceutically acceptable salt thereof.
In some embodiments, the compound is selected from:
| Compound # | Structure |
|---|---|
| 1 | 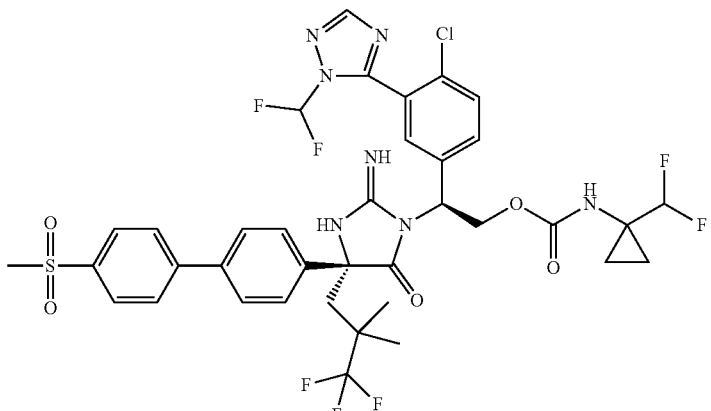 |

-continued

| Compound # | Structure |
|---|---|
| 2 | 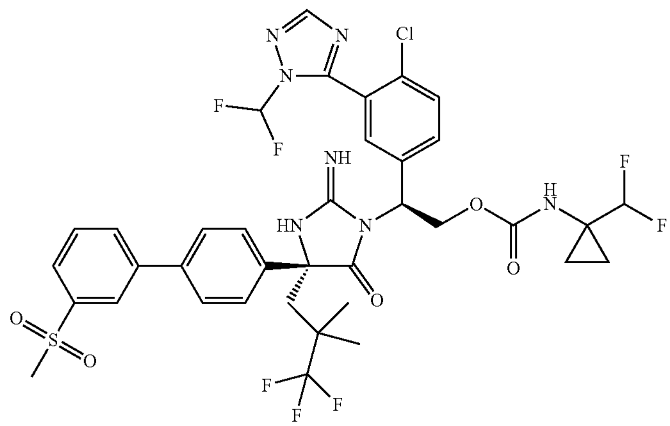 [SMILES: CC(C)(C[C@]1(c2ccc(-c3cccc(S(C)(=O)=O)c3)cc2)NC(=N)N([C@H](COC(=O)NC2(C(F)F)CC2)c2ccc(Cl)c(-c3ncnn3C(F)F)c2)C1=O)C(F)(F)F] |
| 3 | and |
| 4 | | or a pharmaceutically acceptable salt thereof.

In some embodiments, the compound is selected from:
| Compound # | Structure |
| --- | --- |
| 1 | 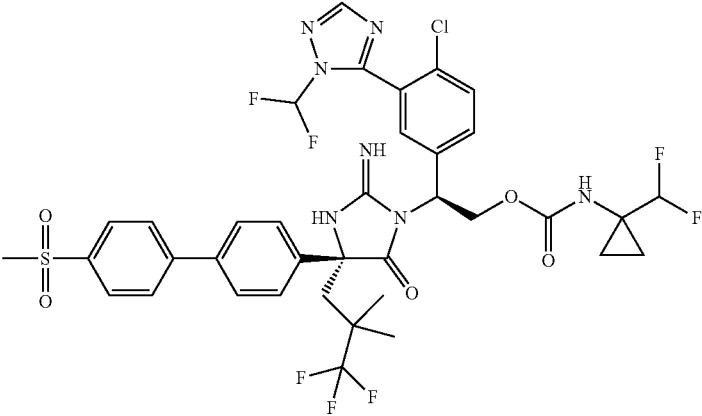 [SMILES: CC(C)(C[C@]1(c2ccc(-c3ccc(S(C)(=O)=O)cc3)cc2)NC(=N)N([C@H](COC(=O)NC2(C(F)F)CC2)c2ccc(Cl)c(-c3ncnn3C(F)F)c2)C1=O)C(F)(F)F] |
| 3 | 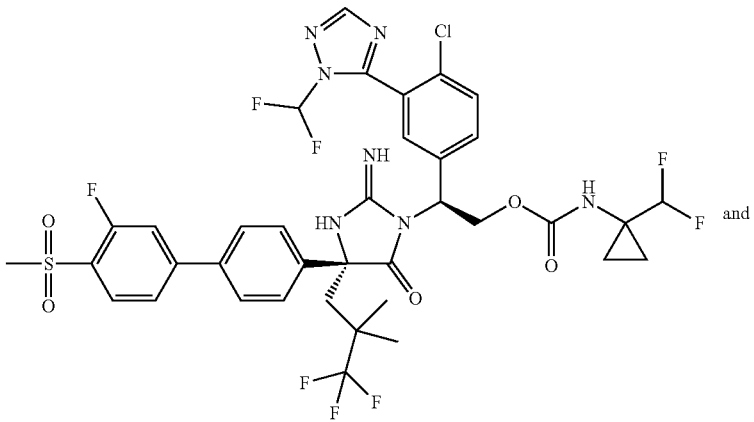 [SMILES: CC(C)(C[C@]1(c2ccc(-c3ccc(S(C)(=O)=O)c(F)c3)cc2)NC(=N)N([C@H](COC(=O)NC2(C(F)F)CC2)c2ccc(Cl)c(-c3ncnn3C(F)F)c2)C1=O)C(F)(F)F] and |
| 4 | 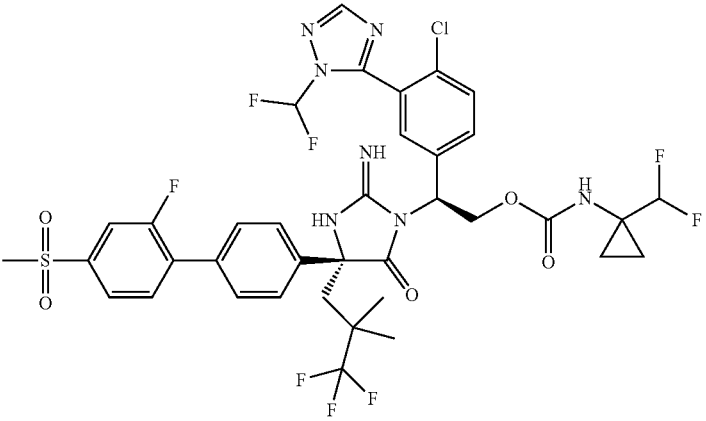 [SMILES: CC(C)(C[C@]1(c2ccc(-c3ccc(S(C)(=O)=O)cc3F)cc2)NC(=N)N([C@H](COC(=O)NC2(C(F)F)CC2)c2ccc(Cl)c(-c3ncnn3C(F)F)c2)C1=O)C(F)(F)F] |
or a pharmaceutically acceptable salt thereof.

In some embodiments, the compound is selected from:

| Compound # | Structure |
|---|---|
| 7 | 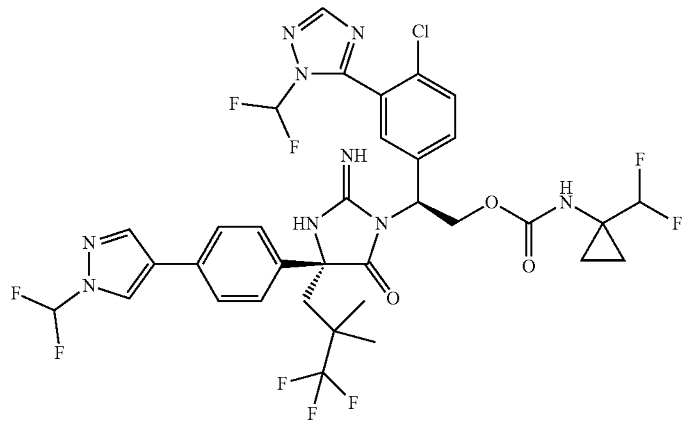 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] |
| 8 | and |
| 9 | | or a pharmaceutically acceptable salt thereof.

In some embodiments, the compound is selected from:

| Compound # | Structure |
|---|---|
| 7 | 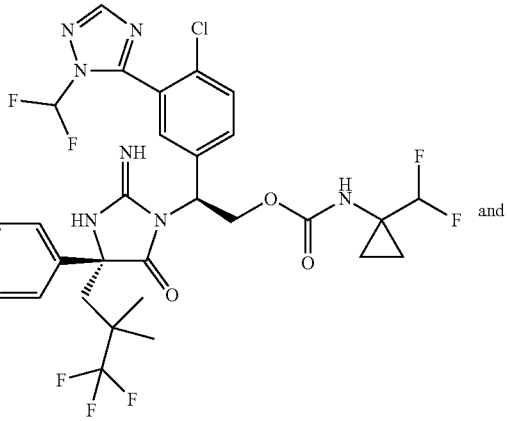 and |
| 8 | 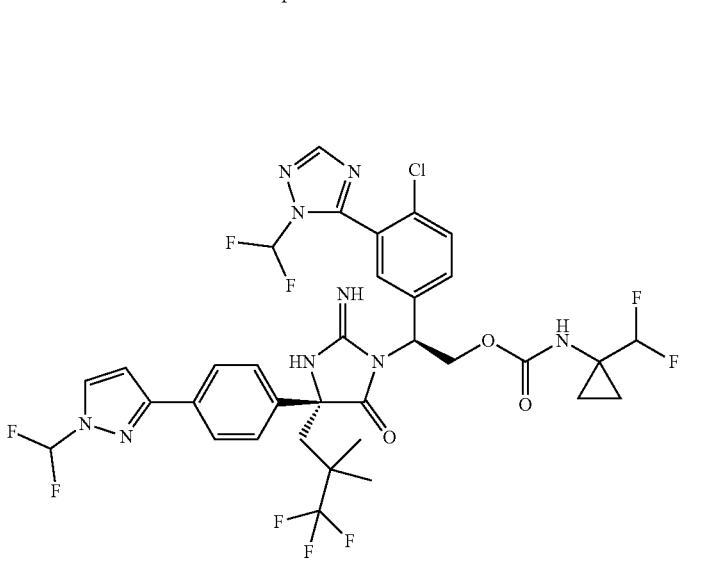 | or a pharmaceutically acceptable salt thereof.

In some embodiments, the compound is Compound 1 having the structure:

Compound 1

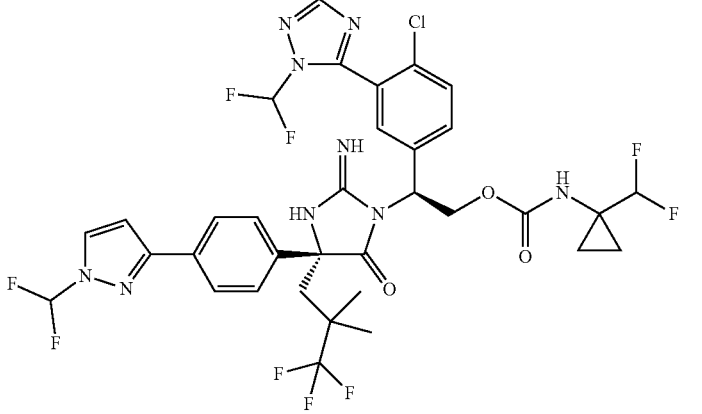

or a pharmaceutically acceptable salt thereof.

In some embodiments, the compound is Compound 2 having the structure:

Compound 2

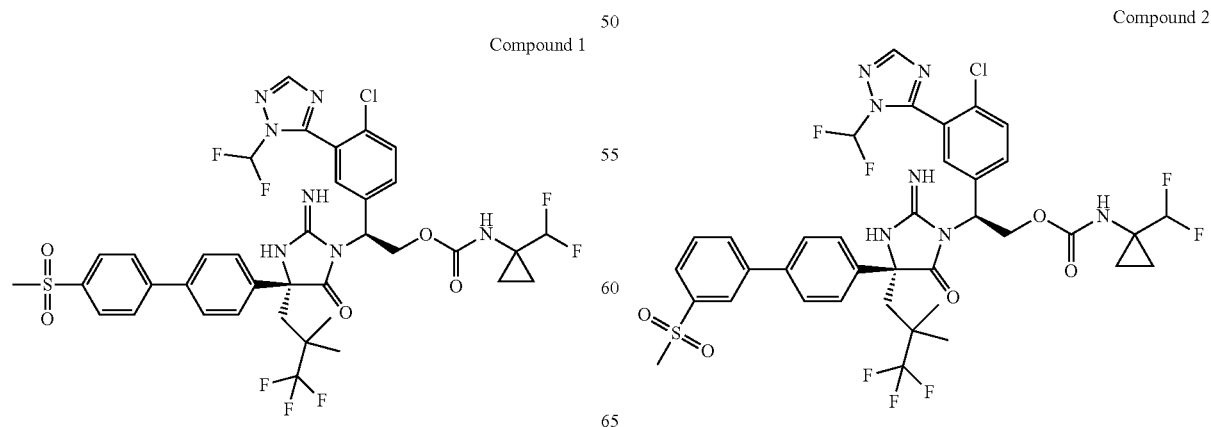

or a pharmaceutically acceptable salt thereof.

In some embodiments, the compound is Compound 3 having the structure:

Compound 3

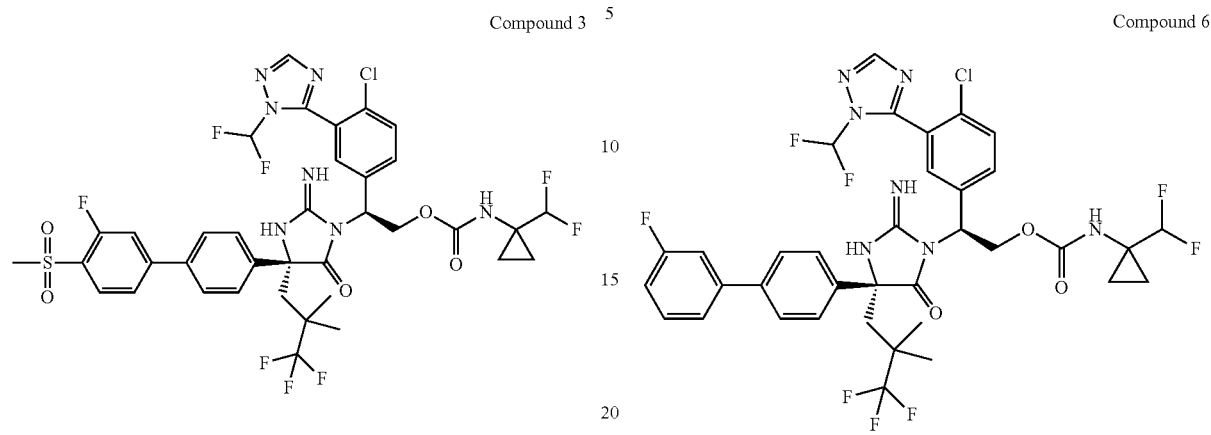

or a pharmaceutically acceptable salt thereof.

In some embodiments, the compound is Compound 4 having the structure:

Compound 4

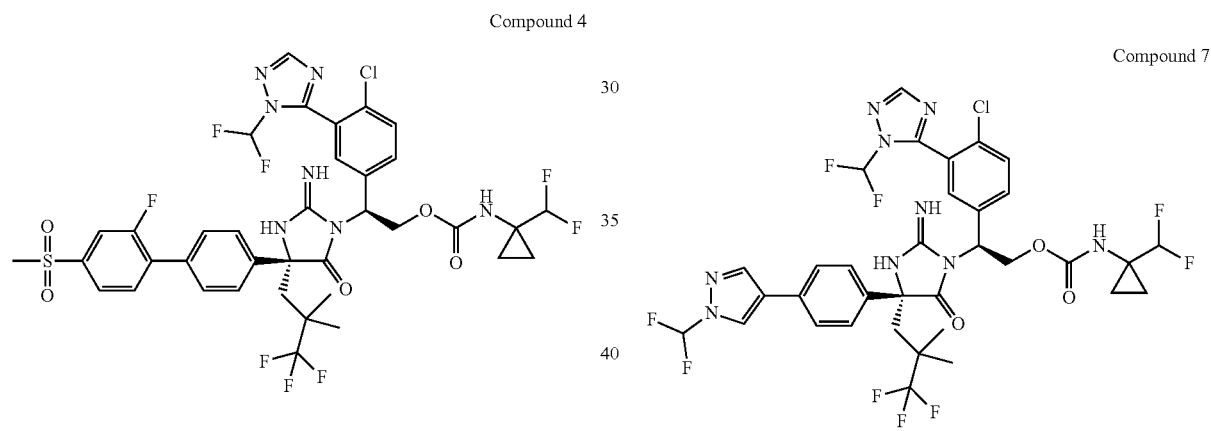

or a pharmaceutically acceptable salt thereof.

In some embodiments, the compound is Compound 5 having the structure:

Compound 5

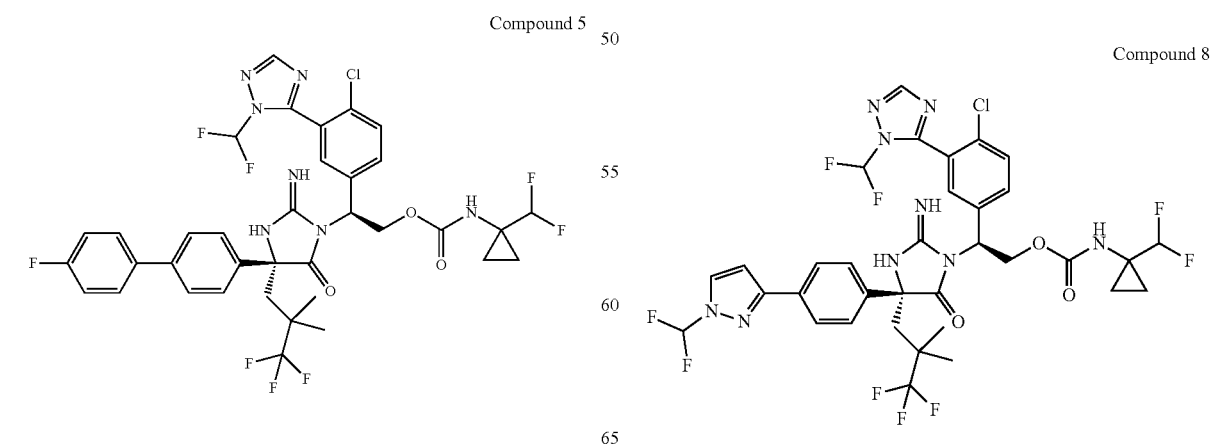

or a pharmaceutically acceptable salt thereof.

In some embodiments, the compound is Compound 6 having the structure:

Compound 6 or a pharmaceutically acceptable salt thereof.

In some embodiments, the compound is Compound 7 having the structure:

Compound 7 or a pharmaceutically acceptable salt thereof.

In some embodiments, the compound is Compound 8 having the structure:

Compound 8 or a pharmaceutically acceptable salt thereof.

In some embodiments, the compound is Compound 9 having the structure:

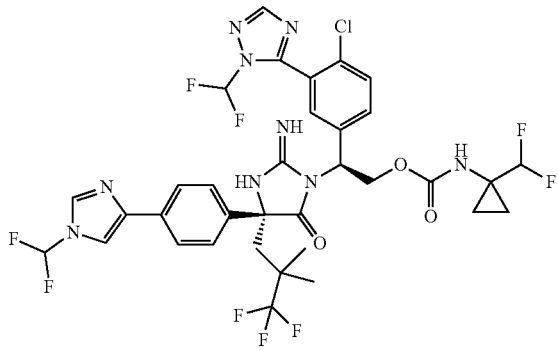

Compound 9 or a pharmaceutically acceptable salt thereof.

The pharmaceutical compositions of compounds provided herein may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound disclosed herein, or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound provided herein, or a pharmaceutically acceptable salt, can be formulated so as to provide quick, sustained or delayed release of the active ingredient after administration to the subject by employing procedures known in the art. Controlled-release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of provided herein, or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shell, acetyl alcohol, and cellulose acetate.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found, e.g., in Handbook of Pharmaceutical Excipients (eds. Rowe, Sheskey & Quinn), 6th edition 2009.

In certain embodiments, a method of treating or preventing a human immunodeficiency virus (HIV) infection comprising administering a therapeutically effective amount of a compound disclosed herein, or a pharmaceutically acceptable salt thereof, to a subject in need thereof, is provided. In certain embodiments, a method of treating a human immunodeficiency virus (HIV) infection comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one or more (e.g., one, two, three, one or two, or one to three) additional therapeutic agents. In certain embodiments, the subject is at risk of contracting the HIV virus, such as a subject who has one or more risk factors known to be associated with contracting the HIV virus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment.

In certain embodiments, a method of treating or preventing a coronavirus infection comprising administering a therapeutically effective amount of a compound disclosed herein, or a pharmaceutically acceptable salt thereof, to a subject in need thereof, is provided. In certain embodiments, a method of treating a coronavirus infection comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one or more (e.g., one, two, three, one or two, or one to three) additional therapeutic agents. In certain embodiments, the subject is at risk of contracting the coronavirus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

In certain embodiments, a method of treating or preventing a human immunodeficiency virus (HIV) infection or coronavirus infection comprising administering a therapeutically effective amount of a compound disclosed herein, or a pharmaceutically acceptable salt thereof, to a subject in need thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, a long-acting HIV regimen, a contraceptive agent, or any combinations thereof, is provided. In certain embodiments, the one or more (e.g., one, two, three, or four; or one or two; or one to three; or one to four) additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof. In certain embodiments, the one or more additional therapeutic agent does not include a pharmacokinetic enhancer.

In some embodiments, the one or more (e.g., one, two, three, or four; or one or two; or one to three; or one to four) additional therapeutic agents are selected from the group consisting of combination drugs for HIV, other drugs for treating HIV, HIV nucleoside reverse transcriptase translocation inhibitors, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof. In some embodiments, the one or more (e.g., one, two, three, or four; or one or two; or one to three; or one to four) additional therapeutic agents are selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), engineered T cell receptors, TCR-T, and combinations thereof.

In some embodiments, the one or more (e.g., one, two, three, or four; or one or two; or one to three; or one to four) additional therapeutic agents are selected from the group consisting of an antiviral agent, a 5-substituted 2'-deoxyuridine analogue, a nucleoside analogue, a pyrophosphate analogue, a nucleoside reverse transcriptase inhibitor, a non-nucleoside reverse transcriptase inhibitor, a protease inhibitor, an integrase inhibitor, an entry inhibitor, an acyclic guanosine analogue, an acyclic nucleoside phosphonate analogue, a HCV NS5A/NS5B inhibitor, an influenza virus inhibitor, an interferon, an immunostimulatory agent, an agent for treatment of RSV, an agent for treatment of picornavirus, an agent for treatment of malaria, an agent for treatment of coronavirus, an agent for treatment of ebola virus, an agent for treatment of HCV, a NS5A inhibitor, an anti-HBV agent, an agent for treatment of HIV, a KRAS inhibitor, a proteasome inhibitor, a vaccine, an antibody, a polymerase inhibitor.

In certain embodiments, a method for inhibiting the replication of the HIV virus, treating AIDS or delaying the onset of AIDS in a subject (e.g., a human), comprising administering a compound disclosed herein, or a pharmaceutically acceptable salt thereof, to the subject is disclosed.

In certain embodiments, a method for inhibiting the replication of a coronavirus, treating a coronavirus, or delaying the onset of a coronavirus related symptom in a subject (e.g., a human), comprising administering a compound disclosed herein, or a pharmaceutically acceptable salt thereof, to the subject is disclosed. In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In certain embodiments, a compound disclosed herein, or a pharmaceutically acceptable salt thereof, for use in medical therapy of an HIV infection (e.g., HIV-1) or the replication of the HIV virus (e.g., HIV-1) or AIDS or delaying the onset of AIDS in a subject (e.g., a human) is disclosed.

In certain embodiments, a compound disclosed herein, or a pharmaceutically acceptable salt thereof, for use in medical therapy of a coronavirus infection, or the replication of a coronavirus, or COVID-19, or delaying the onset of COVID-19 in a subject (e.g., a human) is disclosed. In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In certain embodiments, a compound disclosed herein, or a pharmaceutically acceptable salt thereof, for use in the manufacture of a medicament for treating an HIV infection or the replication of the HIV virus or AIDS or delaying the onset of AIDS in a subject (e.g., a human) is disclosed. One embodiment relates to a compound disclosed herein, or a pharmaceutically acceptable salt thereof, for use in the prophylactic or therapeutic treatment of an HIV infection or AIDS or for use in the therapeutic treatment or delaying the onset of AIDS.

In certain embodiments, a compound disclosed herein, or a pharmaceutically acceptable salt thereof, for use in the manufacture of a medicament for treating a coronavirus infection, or the replication of a coronavirus, or COVID-19, or delaying the onset of COVID-19 related symptoms in a subject (e.g., a human) is disclosed. One embodiment relates to a compound disclosed herein, or a pharmaceutically acceptable salt thereof, for use in the prophylactic or therapeutic treatment of a coronavirus infection or for use in the therapeutic treatment or delaying the onset of coronavirus related symptoms. In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In certain embodiments, the use of a compound disclosed herein, or a pharmaceutically acceptable salt thereof, for the manufacture of a medicament for an HIV infection in a subject (e.g., a human) is disclosed. In certain embodiments, a compound disclosed herein, or a pharmaceutically acceptable salt thereof, for use in the prophylactic or therapeutic treatment of an HIV infection is disclosed.

In certain embodiments, the use of a compound disclosed herein, or a pharmaceutically acceptable salt thereof, for the manufacture of a medicament for a coronavirus infection in a subject (e.g., a human) is disclosed. In certain embodiments, a compound disclosed herein, or a pharmaceutically acceptable salt thereof, for use in the prophylactic or therapeutic treatment of a coronavirus infection is disclosed. In certain embodiments, the coronavirus infection is an infection caused by the SARS virus, the MERS virus, or the 2019-nCoV (COVID-19) virus. In certain embodiments, the coronavirus infection is an infection caused by the SARS virus. In certain embodiments, the coronavirus infection is an infection caused by the MERS virus. In certain embodiments, the coronavirus infection is an infection caused by the 2019-nCoV (COVID-19) virus.

In certain embodiments, in the methods of use, the administration is to a subject (e.g., a human) in need of the treatment. In certain embodiments, in the methods of use, the administration is to a subject (e.g., a human) who is at risk of developing AIDS.

In certain embodiments, in the methods of use, the administration is to a subject (e.g., a human) in need of the treatment. In certain embodiments, in the methods of use, the administration is to a subject (e.g., a human) who is at risk of developing symptoms related to a coronavirus infection. In certain embodiments, the coronavirus infection is an infection caused by the SARS virus, the MERS virus, or the 2019-nCoV (COVID-19) virus. In certain embodiments, the coronavirus infection is an infection caused by the SARS virus. In certain embodiments, the coronavirus infection is an infection caused by the MERS virus. In certain embodiments, the coronavirus infection is an infection caused by the 2019-nCoV (COVID-19) virus.

The compounds disclosed herein, or a pharmaceutically acceptable salt thereof, for use in therapy are provided. In one embodiment, a compound disclosed herein, or a pharmaceutically acceptable salt thereof, is for use in a method of treating an HIV infection or the replication of the HIV virus or AIDS or delaying the onset of AIDS in a subject (e.g., a human). In another embodiment, a compound disclosed herein, or a pharmaceutically acceptable salt thereof, is for use in a method of treating a coronavirus infection, or the replication of a coronavirus, or coronavirus related symptoms, or delaying the onset of coronavirus related symptoms in a subject (e.g., a human). In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

The compounds disclosed herein, or a pharmaceutically acceptable salt thereof, for use in a method of treating or preventing HIV infection in a subject in need thereof are provided. In certain embodiments, a compound disclosed herein, or a pharmaceutically acceptable salt thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

The compounds disclosed herein, or a pharmaceutically acceptable salt thereof, for use in a method of treating or preventing a coronavirus infection in a subject in need thereof are provided. In certain embodiments, a compound disclosed herein, or a pharmaceutically acceptable salt thereof, for use in a method of treating a coronavirus infection in a subject in need thereof is provided. In certain embodiments, the subject in need thereof is a human who has been infected with a coronavirus. In certain embodiments, the subject in need thereof is a human who has been infected with a coronavirus but who has not developed a coronavirus infection related symptom. In certain embodiments, the subject in need thereof is a subject at risk for developing a coronavirus infection related symptom. In certain embodiments, the subject in need thereof is a human who has been infected with a coronavirus and who has developed a coronavirus infection related symptom. In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In one embodiment, a compound disclosed herein, or a pharmaceutically acceptable salt thereof, in combination with one or more (e.g., one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, a long-acting HIV regimen, a contraceptive agent, and any combinations thereof. In certain embodiments, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and any combinations thereof. In certain embodiments, said additional therapeutic agents are selected from the group consisting of combination drugs for HIV, other drugs for treating HIV, HIV nucleoside reverse transcriptase translocation inhibitors, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof. In certain embodiments, said additional therapeutic agents are selected from the group consisting of immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), engineered T cell receptors, TCR-T, and combinations thereof.

In one embodiment, a compound disclosed herein, or a pharmaceutically acceptable salt thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a compound disclosed herein, or a pharmaceutically acceptable salt thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In one embodiment, a compound disclosed herein, or a pharmaceutically acceptable salt thereof, in combination with one or more (e.g., one, two, three, or four; or one or two; or one to three; or one to four) additional therapeutic agents as described herein for use in a method of treating or preventing a coronavirus infection in a subject in need thereof is provided. In one embodiment, said additional therapeutic agents are selected from the group consisting of an antiviral agent, a 5-substituted 2'-deoxyuridine analogue, a nucleoside analogue, a pyrophosphate analogue, a nucleoside reverse transcriptase inhibitor, a non-nucleoside reverse transcriptase inhibitor, a protease inhibitor, an integrase inhibitor, an entry inhibitor, an acyclic guanosine analogue, an acyclic nucleoside phosphonate analogue, a HCV NS5A/NS5B inhibitor, an influenza virus inhibitor, an interferon, an immunostimulatory agent, an agent for treatment of RSV, an agent for treatment of picornavirus, an agent for treatment of malaria, an agent for treatment of coronavirus, an agent for treatment of ebola virus, an agent for treatment of HCV, a NS5A inhibitor, an anti-HBV agent, an agent for treatment of HIV, a KRAS inhibitor, a proteasome inhibitor, a vaccine, an antibody, and a polymerase inhibitor.

In a particular embodiment, a compound disclosed herein or a pharmaceutically acceptable salt thereof, are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound disclosed herein, or a pharmaceutically acceptable salt thereof. In certain embodiments, methods for reducing the risk of acquiring HIV (e.g., HIV-1 and/or HIV-2) comprise administration of a compound disclosed herein, or a pharmaceutically acceptable salt thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of the compound disclosed herein, or pharmaceutically acceptable salt thereof, and a pharmaceutically acceptable excipient.

In certain embodiments, methods for reducing the risk of acquiring HIV (e.g., HIV-1 and/or HIV-2) comprise administration of a compound of disclosed herein, or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In a particular embodiment, a compound disclosed herein, or a pharmaceutically acceptable salt thereof, are provided for use to prevent a coronavirus infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring a coronavirus (e.g., MERS, SARS, or COVID-19) are provided. For example, methods for reducing the risk of acquiring a coronavirus (e.g., MERS, SARS, or COVID-19) comprise administration of a compound disclosed herein, or a pharmaceutically acceptable salt thereof. In certain embodiments, methods for reducing the risk of acquiring a coronavirus (e.g., MERS, SARS, or COVID-19) comprise administration of a compound disclosed herein, or a pharmaceutically acceptable salt thereof, in combination with one or more additional therapeutic agents. In certain embodiments, methods for reducing the risk of acquiring a coronavirus (e.g., MERS, SARS, or COVID-19) comprise administration of a pharmaceutical composition comprising a therapeutically effective amount of the compound disclosed herein, or pharmaceutically acceptable salt thereof, and a pharmaceutically acceptable excipient.

In certain embodiments, the reduction in risk of acquiring a coronavirus is at least about 40%, 50%, 60%, 70%, 80%, 90%, or 95%. In certain embodiments, the reduction in risk of acquiring a coronavirus is at least about 75%. In certain embodiments, the reduction in risk of acquiring a coronavirus is about 80%, 85%, or 90%. In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In the methods of the present invention for the treatment of a coronavirus infection, the compounds of the present invention can be administered at any time to a human who may come into contact with humans suffering from a coronavirus infection or is already suffering from a coronavirus infection. In some embodiments, the compounds of the present invention can be administered prophylactically to humans coming into contact with humans suffering from a coronavirus infection or at risk of coming into contact with humans suffering from a coronavirus infection, e.g., healthcare providers. In some embodiments, administration of the compounds of the present invention can be to humans testing positive for a coronavirus infection but not yet showing symptoms of the coronavirus infection. In some embodiments, administration of the compounds of the present invention can be to humans upon commencement of symptoms of a coronavirus infection. In certain embodiments, the coronavirus infection is an infection caused by the SARS virus, the MERS virus, or the 2019-nCoV (COVID-19) virus. In certain embodiments, the coronavirus infection is an infection caused by the SARS virus. In certain embodiments, the coronavirus infection is an infection caused by the MERS virus. In certain embodiments, the coronavirus infection is an infection caused by the 2019-nCoV (COVID-19) virus.

In some embodiments, the methods disclosed herein comprise event driven administration of a compound provided herein, or a pharmaceutically acceptable salt thereof, to the subject.

As used herein, the terms "event driven" or "event driven administration" refer to administration of a compound provided herein, or a pharmaceutically acceptable salt thereof, (1) prior to an event (e.g., 2 hours, 1 day, 2 days, 5 day, or 7 or more days prior to the event) that would expose the individual to a coronavirus (or that would otherwise increase the individual's risk of acquiring a coronavirus); and/or (2) during an event (or more than one recurring event) that would expose the individual to a coronavirus (or that would otherwise increase the individual's risk of acquiring a coronavirus); and/or (3) after an event (or after the final event in a series of recurring events) that would expose the individual to a coronavirus (or that would otherwise increase the individual's risk of acquiring a coronavirus). In some embodiments, the event driven administration is performed pre-exposure of the subject to the coronavirus. In some embodiments, the event driven administration is performed post-exposure of the subject to the coronavirus. In some embodiments, the event driven administration is performed pre-exposure of the subject to the coronavirus and post-exposure of the subject to the coronavirus. In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In certain embodiments, the methods disclosed herein involve administration prior to and/or after an event that would expose the individual to a coronavirus or that would otherwise increase the individual's risk of acquiring a coronavirus, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP). In certain embodiments, the coronavirus is a SARS virus, a MERS virus, or a 2019-nCoV (COVID-19) virus. In certain embodiments, the coronavirus is a SARS virus. In certain embodiments, the coronavirus is a MERS virus. In certain embodiments, the coronavirus is a 2019-nCoV (COVID-19) virus.

In some embodiments, a compound provided herein, or a pharmaceutically acceptable salt thereof, is administered before exposure of the subject to a coronavirus (e.g., a MERS, SARS, or COVID-19 virus).

In some embodiments, a compound provided herein, or a pharmaceutically acceptable salt thereof, is administered before and after exposure of the subject to a coronavirus (e.g., a MERS, SARS, or COVID-19 virus).

In some embodiments, a compound provided herein, or a pharmaceutically acceptable salt thereof, is administered after exposure of the subject to a coronavirus (e.g., a MERS, SARS, or COVID-19 virus).

The effective dose of a compound of the present invention for treating a coronavirus infection can depend on whether the dose is to be used prophylactically or to treat a human already suffering from 2019-nCoV infection. Moreover, the dose can depend on whether the human suffering from 2019-nCoV infection does not yet show symptoms or is already showing symptoms of 2019-nCoV infection. Larger doses may be necessary for treating humans testing positive for 2019-nCoV infection and for humans showing symptoms of 2019-nCoV infection as compared to humans receiving prophylactic treatment. In certain embodiments, the coronavirus infection is an infection caused by the SARS virus, the MERS virus, or the 2019-nCoV (COVID-19) virus. In certain embodiments, the coronavirus infection is an infection caused by the SARS virus. In certain embodiments, the coronavirus infection is an infection caused by the MERS virus. In certain embodiments, the coronavirus infection is an infection caused by the 2019-nCoV (COVID-19) virus.

Any suitable period of time for administration of the compounds provided herein is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated. The time for administration can depend on whether the compound is being administered prophylactically or to treat a human suffering from a coronavirus infection. For example, a prophylactic administration can be for a period of time while the human is in regular contact with other humans suffering from a coronavirus infection, and for a suitable period of time following the last contact with a human suffering from a coronavirus infection. For humans already suffering from a coronavirus infection, the period of administration can be for any length of time necessary to treat the patient and a suitable period of time following a negative test for a coronavirus infection to ensure the coronavirus infection does not return. In certain embodiments, the coronavirus infection is an infection caused by the SARS virus, the MERS virus, or the 2019-nCoV (COVID-19) virus. In certain embodiments, the coronavirus infection is an infection caused by the SARS virus. In certain embodiments, the coronavirus infection is an infection caused by the MERS virus. In certain embodiments, the coronavirus infection is an infection caused by the 2019-nCoV (COVID-19) virus.

In another embodiment, the use of a compound disclosed herein, or a pharmaceutically acceptable salt thereof, for the manufacture of a medicament for the treatment of an HIV infection in a human being having or at risk of having the infection is disclosed.

Also disclosed herein is a compound disclosed herein, or a pharmaceutically acceptable salt thereof, for use in the therapeutic treatment or delaying the onset of AIDS.

Also disclosed herein is a compound disclosed herein, or a pharmaceutically acceptable salt thereof, for use in the prophylactic or therapeutic treatment of an HIV infection.

In another embodiment, the use of a compound disclosed herein, or a pharmaceutically acceptable salt thereof, for the manufacture of a medicament for the treatment of a coronavirus infection in a human being having or at risk of having the infection is disclosed. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

Also disclosed herein is a compound disclosed herein, or a pharmaceutically acceptable salt thereof, for use in the therapeutic treatment or delaying the onset of symptoms related to a coronavirus infection. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

Also disclosed herein is a compound disclosed herein, or a pharmaceutically acceptable salt thereof, for use in the prophylactic or therapeutic treatment of a coronavirus infection. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

In certain embodiments, a compound disclosed herein, or a pharmaceutically acceptable salt thereof can be used as a research tool (e.g., to study the inhibition of HIV reverse transcriptase in a subject or in vitro).

Kits that include a compound provided herein, or a pharmaceutically acceptable salt, thereof, and suitable packaging are provided. In one embodiment, a kit further includes instructions for use. In one aspect, a kit includes a compound provided herein, or a pharmaceutically acceptable salt thereof, and instructions for use of the compounds in the treatment of the diseases or conditions described herein.

Articles of manufacture that include a compound provided herein, or a pharmaceutically acceptable salt thereof, in a suitable container are provided. The container may be a vial, jar, ampoule, preloaded syringe, and intravenous bag.

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, a method for treating or preventing a coronavirus infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating a coronavirus infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

In one embodiment, pharmaceutical compositions comprising a compound disclosed herein, or a pharmaceutically acceptable salt thereof, in combination with one or more (e.g., one, two, three, one or two, or one to three) additional acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the present disclosure provides a method for treating a coronavirus infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating a coronavirus infection. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV or Coronavirus Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of provided herein is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, a compound of provided herein is formulated as a tablet, which may optionally contain one or more other compounds useful for treating a coronavirus. dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

In certain embodiments, such tablets are suitable for once daily dosing.

HIV Combination Therapy

In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TAL-ENs), cell therapies (such as chimeric antigen receptor T-cell, CAR-T, and engineered T cell receptors, TCR-T, autologous T cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, a long-acting HIV regimen, a contraceptive agent, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine);

BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

Other HIV Drugs

Examples of other drugs for treating HIV include acemannan, alisporivir, astodrimer, BanLec, CC-11050, deferiprone, Gamimune, griffithsin, metenkefalin, naltrexone, Prolastin, REP 9, RPI-MN, Vorapaxar, VSSP, H1viral, SB-728-T, 1,5-dicaffeoylquinic acid, rHIV7-shl-TAR-CCR5RZ, MazF gene therapy, MK-8527, BlockAide, PSC-RANTES, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, and elsulfavirine (VM-1500). Further examples of non-nucleoside reverse transcriptase inhibitors are disclosed in U.S. Patent Publication No. US2016/0250215.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include ceniviroc, CCR5 inhibitors, gp41 inhibitors, CD4 attachment inhibitors, DS-003 (BMS-599793), gp120 inhibitors, and CXCR4 inhibitors.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176, BMS-986197, GSK-3640254 and GSK-2838232.

Latency Reversing Agents

Examples of latency reversing agents include histone deacetylase (HDAC) inhibitors, proteasome inhibitors such as velcade, and ixazomib citrate, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), IL-15 modulating antibodies, JQ1, disulfiram, amphotericin B, and ubiquitin inhibitors such as largazole analogs, APH-0812, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207, AVI-621, AVI-101, AVI-201, AVI-301, and AVI-CAN1-15 series.

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (PD-1) modulators; programmed death-ligand 1 (PD-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107; interleukin-15/Fc fusion protein; AM-0015; ALT-803; NIZ-985; NKTR-255; NKTR-262; NKTR-214; normferon; peginterferon alfa-2a; peginterferon alfa-2b; recombinant interleukin-15; Xmab-24306, RPI-MN; STING modulators; RIG-I modulators; NOD2 modulators; SB-9200, and IR-103.

Examples of TLR agonists include vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod, and RO-7020531.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bnABs (broadly neutralizing HIV-1 antibodies), BMS-936559, TMB-360, and those targeting HIV gp120 or gp41, antibody-recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Examples of those targeting HIV in such a manner include bavituximab, UB-421, C2F5, 2G12, C4E10, C2F5+C2G12+C4E10, 8ANC195, 3BNC117, 3BNC117-LS, 3BNC60, D1D2, 10-1074, 10-1074-LS, GS-9722, DH411-2, BG18, PGT145, PGT121, PGT122, PGT-151, PGT-133, PGT-135, PGT-128, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PG9, PG16, 8ANC195, 2Dm2m, 4Dm2m, 6Dm2m, VRC-01, VRC-01-LS, PGDM1400, A32, 7B2, 10E8, 10E8VLS, 3810109, 10E8v4, 10E8.4/iMab, VRC-01/PGDM-1400/10E8v4, IMC-HIV, iMabm36, 10E8v4/PGT121-VRC01, eCD4-Ig, IOMA, CAP256-VRC26.25, DRVIA7, SAR-441236, VRC-07-523, VRC07-523LS, VRC-HIVMAB080-00-AB, VRC-HIVMAB060-00-AB, P2G12, and VRC07. Example of HIV bispecific antibodies include MGD014 and TMB-bispecific.

Example of in vivo delivered bnABs include AAV8-VRC07; and mRNA encoding anti-HIV antibody VRC01.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines using viral vectors such as arenavirus, lymphocytic choriomeningitis virus (LCMV), pichinde virus, modified vaccinia Ankara virus (MVA), adenovirus, adeno-associated virus (AAV), vesicular stomatitis virus (VSV) and Chimpanzee adenovirus (ChAd), DNA vaccines, CD4-derived peptide vaccines, vaccine combinations, BG505 SOSIP.664 gp140, rgp120 (AIDSVAX), ALVAC HIV, (vCP1521)/AIDSVAX B/E (gp120) (RV144), monomeric gp120 HIV-1 subtype C vaccine, Remune, ITV-1, Contre Vir, Ad4-Env145NFL, Ad5-ENVA-48, HB-500, DCVax-001 (CDX-2401), Vacc-4x, Vacc-05, Vacc-CRX, VVX-004, VAC-3 S, multiclade DNA recombinant adenovirus-5 (rAd5), rAd5 gag-pol env A/B/C vaccine, Pennvax-G, Pennvax-GP/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B 11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG- 17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, HIV-001, and virus-like particle vaccines such as pseudovirion vaccine, CombiVlCHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MI-IC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based immunotherapies (Vaxwave, TheraT), MVA-BN HIV-1 vaccine regimen, MVA.tHIVconsv4, MVA.tHIVconsv3, UBI HIV gp120, mRNA based prophylactic vaccines, TBL-1203HI, VRC-HIVRGP096-00-VP, VAX-3S, and HIV MAG DNA vaccine.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of cell therapy include dendritic cell therapy or T-cell therapy (e.g., CD4-positive T-cells or CD8-positive T-cells).

Examples of a T-cell therapy include a TCR-T cell therapy.

Examples of dendritic cell therapy include AGS-004, C34-CCR5/C34-CXCR4 expressing CD4-positive T cell, and AGT-103-transduced autologous T cell therapy.

Examples of gene editing include CCR5 gene editing drugs (e.g., SB-728T), CCR5 gene inhibitors (e.g., Cal-1), AGT-103-transduced autologous T cell therapy, and AAV-eCD4-Ig gene therapy.

Gene Editors

Genome editing systems include a CRISPR/Cas9 system, a zinc finger nuclease system, a TALEN system, a homing endonucleases system, and a meganuclease system.

Examples of HIV targeting CRISPR/Cas9 systems include EBT-101.

CAR-T Cell Therapy

A CAR-T cell therapy can involve a population of immune effector cells engineered to express a chimeric antigen receptor (CAR), wherein the CAR comprises an HIV antigen-binding domain. The HIV antigen can include an HIV envelope protein or a portion thereof, gp120 or a portion thereof, the CD4 binding site on gp120, the CD4-induced binding site on gp120, N-glycan on gp120, the V2 of gp120, the membrane proximal region on gp41. The immune effector cell can be a T-cell or an NK cell. In some embodiments, the T-cell is a CD4-positive T-cell, a CD8-positive T-cell, or a combination thereof. CAR-T cells can be autologous or allogeneic.

Examples of HIV CAR-T include VC-CAR-T, anti-CD4 CART cell therapy, autologous hematopoietic stem cells genetically engineered to express a CD4 CAR and the C46 peptide.

TCR-T Cell Therapy

TCR-T cells can be engineered to target HIV-derived peptides present on the surface of virus-infected cells.

Long-Acting HIV Regimen

Examples of drugs in development as long acting regimens include cabotegravir LA, rilpivirine LA, cabotegravir LA+rilpivirine LA, any integrase LA, VM-1500A-LAI, maraviroc (LAI), tenofovir implant, MK-8591 implant, long-acting dolutegravir, long acting raltegravir+lamivudine.

Contraceptive Agents

Therapeutic agents used for birth control (contraceptive agent) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); BIKTARVY® (bictegravir, emtricitabine, and tenofovir alafenamide); COMPLERA® (EVIPLERA®, rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein may be combined with one or more additional therapeutic agents in any dosage amount of the compound provided herein (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein may be combined with the agents provided herein in any dosage amount of the compound (e.g., from 1 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Coronavirus Combination Drugs

The compounds described herein can also be used in combination with one or more additional therapeutic agents. As such, also provided herein are methods of treatment of a coronavirus infection, wherein the methods comprise administering to a subject in need thereof a compound of the disclosure and a therapeutically effective amount of an additional therapeutic agent. In certain embodiments, the coronavirus infection is an infection caused by a SARS virus, a MERS virus, or a 2019-nCoV (COVID-19) virus. In certain embodiments, the coronavirus infection is an infection caused by a SARS virus. In certain embodiments, the coronavirus infection is an infection caused by a MERS virus. In certain embodiments, the coronavirus infection is an infection caused by a 2019-nCoV (COVID-19) virus.

Antivirals

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], or a combination thereof.

Nucleoside Analogue

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, or a combination thereof.

Phosphate Analogue

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

Reverse Transcriptase Inhibitor

In some embodiments, the additional therapeutic agent is a nucleoside reverse transcriptase inhibitor. In some embodiments, the antiviral agent is zidovudine, didanosine, zalcitabine, stavudine, lamivudine, abacavir, emtricitabine, or a combination thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

Protease Inhibitor

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of asunaprevir, boceprevir, paritaprevir, simeprevir, telaprevir, vaniprevir, grazoprevir, and combinations thereof Integrase Inhibitor In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of raltegravir, dolutegravir, elvitegravir, and combinations thereof.

Entry Inhibitor

In some embodiments, the additional therapeutic agent is an entry inhibitor. For example, in some embodiments, the additional therapeutic agent is selected from the group consisting of docosanol, enfuvirtide, maraviroc, palivizumab, respiratory syncytial virus immune globulin, intravenous [RSV-IGIV], varicella-zoster immunoglobulin [VariZIG], varicella-zoster immune globulin [VZIG], and combinations thereof.

Acyclic Guanosine Analogues

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

Acyclic Nucleoside Phosphonate Analogues

In some embodiments, the additional therapeutic agent is an acyclic nucleoside phosphonate analogue. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

HCV NS5A/NS5B Inhibitors

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of daclatasvir, ledipasvir, ombitasvir, elbasvir, sofosbuvir, dasabuvir, and combinations thereof.

Influenza Virus Inhibitors

In some embodiments, the additional therapeutic agent is an influenza virus inhibitor. In some embodiments, the additional therapeutic agents is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

Interferons

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. In some embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

Immunostimulatory Agents

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

Anti RSV Agents

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

Anti-Picorna Virus Agents

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

Antimalaria Agents

In some embodiments, the additional therapeutic agent is an agent for treatment of malaria.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

Anti-Coronavirus Agents

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, nafamostat, LB-2, AM-1, anti-viroporins, and combinations thereof.

Anti Ebola Virus Agents

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

Anti HCV Agents

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NSSA inhibitor. For example, in some embodiments, the additional therapeutic agent is selected from the group consisting of ledipasvir, velpatasvir, and combinations thereof.

Anti-HBV Agents

In some embodiments, the additional therapeutic agent is an anti-HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164 (Roche), WO2016023877 (Roche), US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (REPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

Anti HIV Agents

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some examples, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®, rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUIMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some examples, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lamivudine, bictegravir and combinations thereof. In some embodiment, the additional therapeutic agent is bictegravir. In some examples, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof.

In some embodiments, the additional therapeutic agent is a HIV nucleoside reverse transcriptase inhibitor. In some embodiments, the additional therapeutic agent is a HIV nonnucleoside reverse transcriptase inhibitor. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some examples, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp(VM-1500), and combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUIMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

Kinase Inhibitors

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof.

KRAS Inhibitor

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

Proteasome Inhibitor

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. In some embodiments, the additional therapeutic agent is carfilzomib.

Vaccines

In some embodiments, the additional therapeutic agent is a vaccine. For example, in some embodiments, the additional therapeutic agent is a DNA vaccine, RNA vaccine, live-attenuated vaccine, protein-based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vaqta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccines (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239).

Antibodies

In some embodiments, the additional therapeutic agent is an antibody, for example a monoclonal antibody. In some embodiments, the additional therapeutic agent is an antibody that binds to a coronavirus, for example an antibody that binds to SARS or MERS.

Others

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASCO9F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5] decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

Compositions disclosed herein are also used in combination with other active ingredients. For the treatment of COVID-19 virus infections, preferably, the other active therapeutic agent is active against coronavirus infections, for example COVID-19 virus infections. The compounds and compositions provided herein are also intended for use with general care provided patients with COVID-19 viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), immonumodulatory medications (e.g., interferon), other small molecule or biologics antiviral agents targeting COVID-19 (such as but not limited to lopinavir/ritonavir, EIDD-1931, favipiravir, ribavirine, neutralizing antibodies, etc), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

In some embodiments, the additional therapeutic agent is remdesivir.

EXAMPLES

Methods for preparing the novel compounds described herein will be apparent to those of skill in the art with suitable procedures being described, for example, in the reaction schemes and examples below.

Section 1 provides exemplary synthetic schemes for assembling compounds, preparation of intermediates as used herein, example syntheses and compounds. Section 2 shows biological activity.

1. Synthesis Examples

Preparation of Intermediates

Preparation of Isopropyl (R)-2-amino-2-(4-bromophenyl)-5,5,5-trifluoro-4,4-dimethylpentanoate

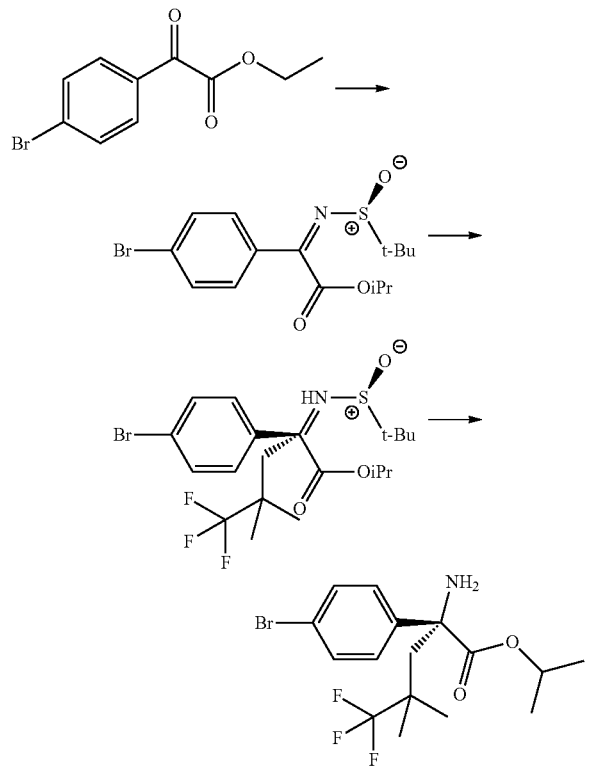

Preparation of isopropyl (S)-2-((tert-butylsulfinyl)imino)-2-(4-bromophenyl)acetate Ti(Oi-Pr)$_4$ (163 mmol) was added dropwise to a stirred solution of ethyl 2-(4-bromophenyl)-2-oxoacetate (136 mmol) and (S)-(−)-2-methyl-2-propanesulfinamide (163 mmol) in n-heptane (350 mL). The mixture was stirred at 80° C. for 12 hr. After cooling to rt, water (500 mL) was added and stirred for 10 min. The biphasic mixture was filtered through Celite, and the filter cake was washed with n-heptane (300 mL). The two layers were separated and the aqueous layer was extracted with dichloromethane (200 mL). The organic layer and the extracts were combined, dried over sodium sulfate, and filtered. The filtrate was concentrated. The residue was purified by silica gel column chromatography (elution gradient 0-2% EtOAc in petroleum ether) to give the product. $^1$H NMR (400 MHz, CDCl$_3$) δ 7.61 (dd, J=8.8 Hz, 4H), 5.40-5.32 (m, 1H), 1.40 (dd, J=6.4 Hz, 6H), 1.33 (s, 9H).

Preparation of isopropyl (R)-2-(4-bromophenyl)-2-(((S)-tert-butylsulfinyl)amino)-5,5,5-trifluoro-4,4-dimethylpentanoate The desired Grignard reagent was prepared by the following procedure: 3-bromo-1,1,1-trifluoro-2,2-dimethylpropane (96.1 mmol) was added dropwise to magnesium turnings at 65° C. 115 mmol; activated with BrCH$_2$CH$_2$Br (5.34 mmol) in THF (60 mL) at 15° C. and stirred for 1 hr. The reaction mixture was cooled to room temperature and this magnesium reagent was ready for use. The magnesium reagent was added dropwise to a solution of isopropyl (S)-2-((tert-butylsulfinyl)imino)-2-(4-bromophenyl)acetate (4.0 g, 10.6 mmol) in dichloromethane (300 mL) at −78° C. and the resulting reaction mixture was stirred at −78° C. for 11 hr. The reaction was quenched with saturated aq NH$_4$Cl solution (100 mL), and the mixture was extracted with dichloromethane (200 mL×2). The organic extracts were combined and concentrated. The residue was purified by silica gel column chromatography (elution gradient 0-20% EtOAc in petroleum ether) to give the product. $^1$H NMR (400 MHz, methanol-d$_4$) δ 7.55 (m, 4H), 5.14-4.87 (m, 1H), 2.80 (d, J=14.8 Hz, 1H), 2.49 (d, J=14.8 Hz, 1H), 1.28 (t, J=6.8 Hz, 6H), 1.23 (s, 9H), 1.04 (s, 3H), 0.88 (s, 3H).

Preparation of isopropyl (R)-2-amino-2-(4-bromophenyl)-5,5,5-trifluoro-4,4-dimethylpentanoate To a solution of isopropyl (R)-2-(4-bromophenyl)-24(S)-tert-butylsulfinyl)amino)-5,5,5-trifluoro-4,4-dimethylpentanoate (15.9 mmol) in dichloromethane (8 mL) was added hydrogen chloride in 1,4-dioxane (4M, 20 mL) at 0° C. and stirred at rt for 1 hr. The mixture was poured into aqueous sodium bicarbonate (200 mL). The mixture was extracted with dichloromethane (100 mL×2). The organic extracts were combined and concentrated. The residue was purified by silica gel column chromatography (elution gradient 0-2% EtOAc in petroleum ether) to give the product (3.9 g, 62%). $^1$H NMR (400 MHz, methanol-d$_4$) δ 7.50 (m, 4H), 4.99-4.90 (m, 1H), 2.61 (d, J=14.8 Hz, 1H), 2.16 (d, J=14.8 Hz, 1H), 1.24 (s, 3H), 1.18 (dd, J$_1$=2.8 Hz, J$_2$=3.6 Hz, 6H), 1.06 (s, 3H).

Preparation of Isopropyl (R)-2-(3-((benzyloxy)carbonyl)thioureido)-2-(4-bromophenyl)-5,5,5-trifluoro-4,4-dimethylpentanoate

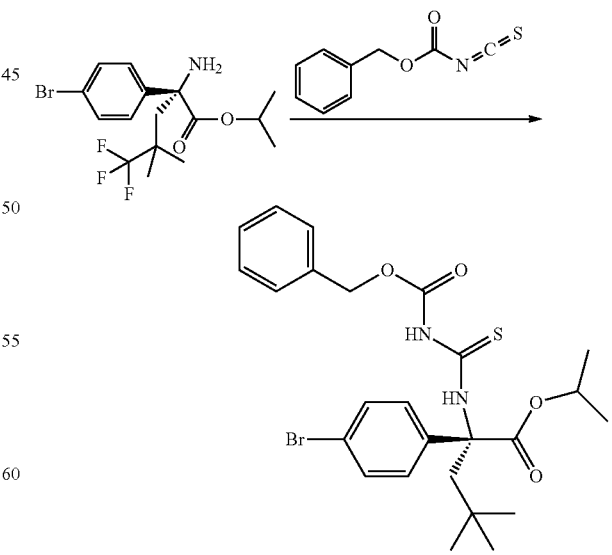

To a gently stirred biphasic solution of isopropyl (R)-2-amino-2-(4-bromophenyl)-5,5,5-trifluoro-4,4-dimethylpentanoate (5.05 mmol) in EtOAc (30 mL) and saturated aqueous sodium bicarbonate (30 mL) was dropwise added a solution of O-benzyl carbonisothiocyanatidate (6.06 mmol) in ethyl acetate (20 mL). The mixture was stirred for 1 hr at rt. The ethyl acetate layer was separated, washed with brine, dried over MgSO$_4$, filtered, and concentrated. The residue was purified by silica gel column chromatography (0-100% ethyl acetate in hexanes) to give the product. LCMS-ESI+ (m/z): calc'd for $C_{25}H_{28}BrF_3N_2O_4S$: 589.1 [M+H]$^+$; found: 588.9 [M+H]$^+$.

Preparation of Tert-Butyl (S)-4-(4-chloro-3-(1-(difluoromethyl)-1H-1,2,4-triazol-5-yl)phenyl)-2,2-dimethyloxazolidine-3-carboxylate

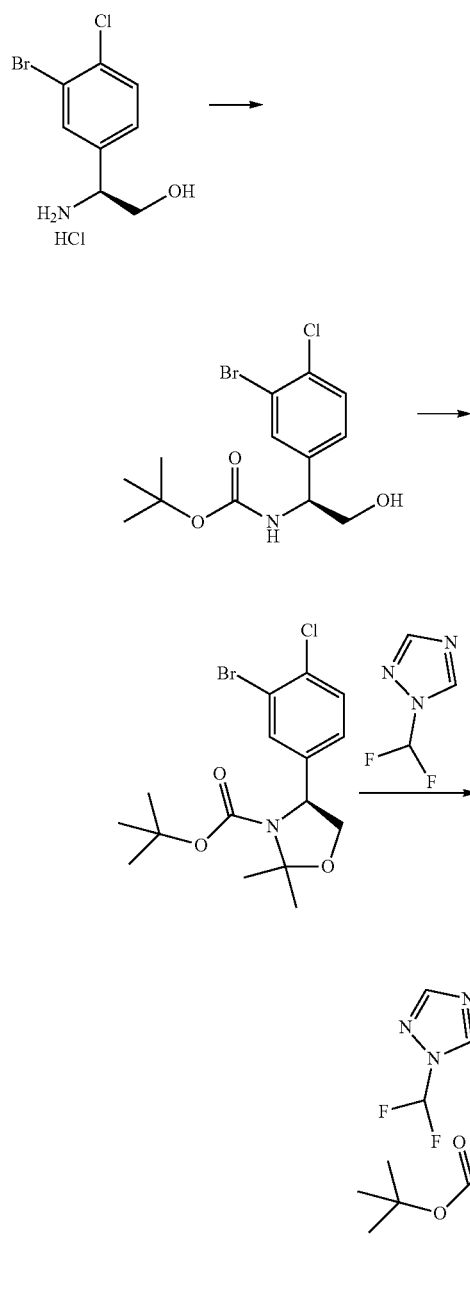

Preparation of tert-butyl (S)-(1-(3-bromo-4-chlorophenyl)-2-hydroxyethyl)carbamate To a solution of (S)-2-amino-2-(3-bromo-4-chlorophenyl)ethan-1-ol hydrochloride (70 mmol) in tetrahydrofuran (200 mL) were sequentially added DIPEA (210 mmol) and Boc$_2$O (16.8 g, 77 mmol). The resulting mixture was stirred for 3 hr at room temperature. The reaction was then quenched by addition of saturated aqueous NH$_4$Cl (200 mL). The resulting solution was extracted with ethyl acetate (200 mL×3). The extracts were combined, washed with brine (200 mL×2), dried over anhydrous sodium sulfate, and concentrated. Hexanes (200 mL) was added and stirred for 30 min. at room temperature. The resulting solid was collected by filtration to afford the product. $^1$H NMR (300 MHz, DMSO-d$_6$) δ 7.67 (d, 1H), 7.57 (d, 1H), 7.31 (dd, 2H), 4.85 (m, 1H), 4.49 (m, 1H), 3.48 (m, 2H), 1.32 (s, 9H).

Preparation of tert-butyl (S)-4-(3-bromo-4-chlorophenyl)-2,2-dimethyloxazolidine-3-carboxylate To a mixture of tert-butyl (S)-(1-(3-bromo-4-chlorophenyl)-2-hydroxyethyl)carbamate (66 mmol), acetone (230 mL) and 2,2-dimethoxypropane (653 mmol) was added BF$_3$.Et$_2$O (0.6 g, 4 mmol) in one portion at room temperature. The resulting solution was stirred for 2 hr at room temperature. The reaction was then quenched by addition of saturated aqueous sodium bicarbonate (300 mL). The resulting mixture was extracted with ethyl acetate (200 mL×3). The organic extracts were combined, washed with brine (300 mL), dried over anhydrous sodium sulfate, and concentrated. The residue was triturated with hexanes (100 mL). The resulting solid was collected by filtration to afford the product. $^1$H NMR (300 MHz, DMSO-d$_6$) δ 7.62 (m, 2H), 7.32 (d, 1H), 4.86 (d, 1H), 4.25 (m, 1H), 3.79 (m, 1H), 1.64 (s, 3H), 1.50 (s, 3H), 1.41 (s, 3H), 1.18 (s, 6H).

Preparation of tert-butyl (S)-4-(4-chloro-3-(1-(difluoromethyl)-1H-1,2,4-triazol-5-yl)phenyl)-2,2-dimethyloxazolidine-3-carboxylate A mixture of tert-butyl (4S)-4-(3-bromo-4-chlorophenyl)-2,2-dimethyl-1,3-oxazolidine-3-carboxylate (10 mmol), 1-(difluoromethyl)-1H-1,2,4-triazole (13 mmol), Pd(OAc)$_2$ (0.50 mmol), n-Bu(Ad)2P-HI (CAS #714951-87-8, 1 mmol), EtMe$_2$CCOOH (3 mmol) and potassium carbonate (30 mmol) in toluene (16 mL) was purged with nitrogen for 15 min. and stirred for 2 days at 120° C. This reaction was conducted 4 more times in parallel. After cooling, the all the reaction mixtures were combined and diluted with ethyl acetate (100 mL). The insoluble was filtered out. The filtrate was concentrated. The residue was diluted with acetonitrile (100 mL) and purified by reverse-phase HPLC (acetonitrile and water with 0.05% ammonium hydroxide) to afford the product (a total of 57%). $^1$H NMR (300 MHz, methanol-d$_4$) δ 8.25 (s, 1H), 7.80-7.13 (m, 4H), 4.92 (m, 1H), 4.33 (dd, J=9.2, 6.7 Hz, 1H), 3.85 (d, J=9.4 Hz, 1H), 1.66 (s, 3H), 1.54 (s, 3H), 1.43 (s, 3H), 1.23 (s, 6H).

Preparation of (S)-2-amino-2-(4-chloro-3-(1-(difluoromethyl)-1H-1,2,4-triazol-5-yl)phenyl)ethyl (1-(difluoromethyl)cyclopropyl)carbamate

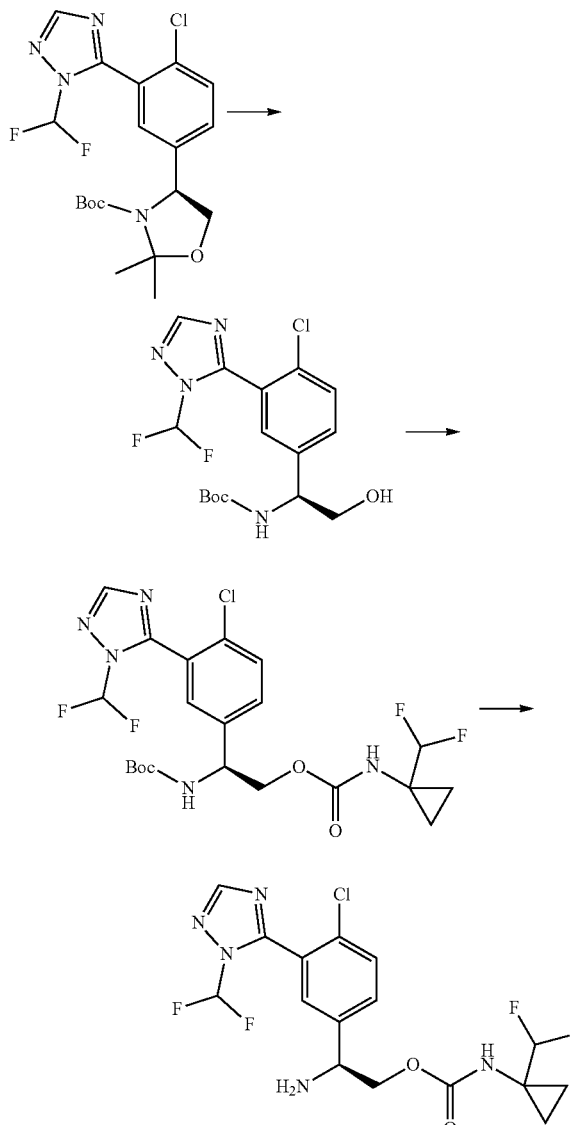

Preparation of tert-butyl (S)-(1-(4-chloro-3-(1-(difluoromethyl)-1H-1,2,4-triazol-5-yl)phenyl)-111-2-hydroxyethyl)carbamate tert-butyl (S)-4-(4-chloro-3-(1-(difluoromethyl)-1H-1,2,4-triazol-5-yl)phenyl)-2,2-dimethyloxazolidine-3-carboxylate (1.52 mmol) was treated with hydrogen chloride in dioxane (4M, 5 mL) at rt for 2 hr. The reaction mixture was concentrated and the residue was dissolved in hydrogen chloride in MeOH (1.25 M, 10 mL). After 16 hr, the reaction mixture was concentrated to dryness, and used directly in the next reaction. The N-Boc-protection was then achieved by using Boc₂O as in the preparation of tert-butyl (S)-(1-(3-bromo-4-chlorophenyl)-2-hydroxyethyl)carbamate.

Preparation of tert-butyl (S)-(1-(4-chloro-3-(1-(difluoromethyl)-1H-1,2,4-triazol-5-yl)phenyl)-2-(((1-(difluoromethyl)cyclopropyl)carbamoyl)oxy)ethyl)carbamate To a solution of 1-(difluoromethyl)-1-isocyanatocyclopropane in toluene (35 mmol in 50 ml toluene) was added a solution of tert-butyl (S)-(1-(4-chloro-3-(1-(difluoromethyl)-1H-1,2,4-triazol-5-yl)phenyl)-2-hydroxyethyl)carbamate (18 mmol) in DCM (20 mL), followed by DIPEA (3.13 mL, 18 mmol). Additional DCM (50 mL) was added. The reaction mixture was stirred at room temperature for 17 hr. The mixture was then concentrated, and the residue was purified by silica gel column chromatography (0-100% EtOAc/hexanes) to give the product.

Preparation of (S)-2-amino-2-(4-chloro-3-(1-(difluoromethyl)-1H-1,2,4-triazol-5-yl)phenyl)ethyl (1-(difluoromethyl)cyclopropyl)carbamate A solution of tert-butyl (S)-(1-(4-chloro-3-(1-(difluoromethyl)-1H-1,2,4-triazol-5-yl)phenyl)-2-(((1-(difluoromethyl)cyclopropyl)carbamoyl)oxy)ethyl)carbamate (13.4 mmol) in TFA (100 mL) was stirred at rt for 2 hr. The mixture was then concentrated to dryness. The crude material was absorbed on silica gel and loaded onto a short silica gel column. Elution with 0-50% EtOAc/hexanes removed light yellow impurities. Then, elution with 10% MeOH in EtOAc afforded the desired free base product.

Preparation of 1-(difluoromethyl)-1-isocyanatocyclopropane

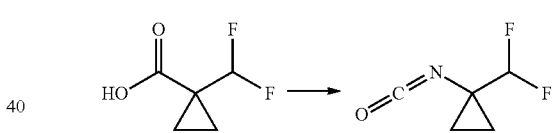

To a 2000-mL 3-necked round-bottom flask, purged and maintained with an inert atmosphere of nitrogen, were placed a solution of 1-(difluoromethyl)cyclopropane-1-carboxylic acid (265 mmol) in toluene (1000 mL), DPPA (278 mmol) and TEA (291 mmol). The mixture was stirred for 3 hr at 100° C. The crude product was purified by atmospheric distillation. Fractions containing the desired product were collected at −110° C., and used directly for the next step.

Preparation of 1-(difluoromethyl)-1H-1,2,4-triazole

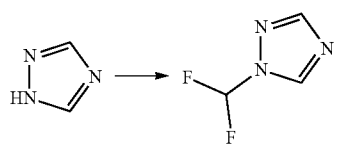 [SMILES: c1nc[nH]n1 ; FC(F)n1cncn1]

To a mixture of 1H-1,2,4-triazole (724 mmol), benzyltriethylammonium chloride (31 mmol) in dichloromethane (1000 mL) in a 2 L 3-necked round-bottom flask was added a solution of potassium hydroxide (1.44 mol) in water (100 mL) in one portion. The flask was evacuated and backfilled with $CHClF_2$ (g) (×3). The resulting solution was stirred for 24 hr at 35° C. The reaction mixture was then cooled to room temperature. The resulting mixture was concentrated. The residue was purified by distillation under reduced pressure (35 mm Hg) and the fractions were collected at 68° C. to afford the product.

Preparation of (S)-24(R)-2-(((benzyloxy)carbonyl)imino)-4-(4-bromophenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate

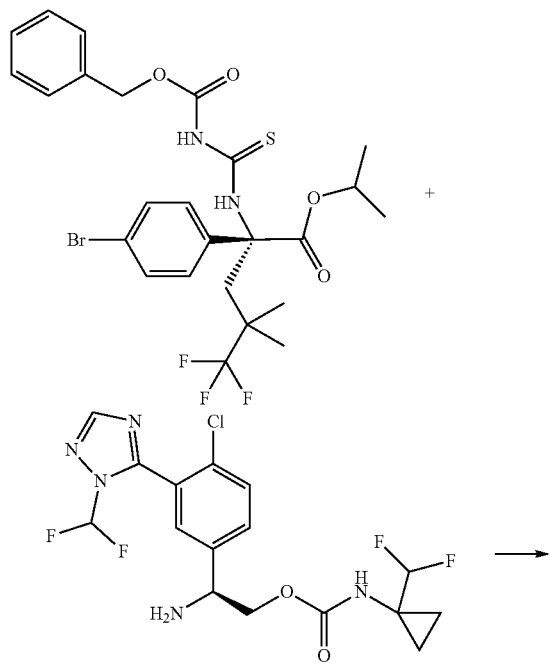

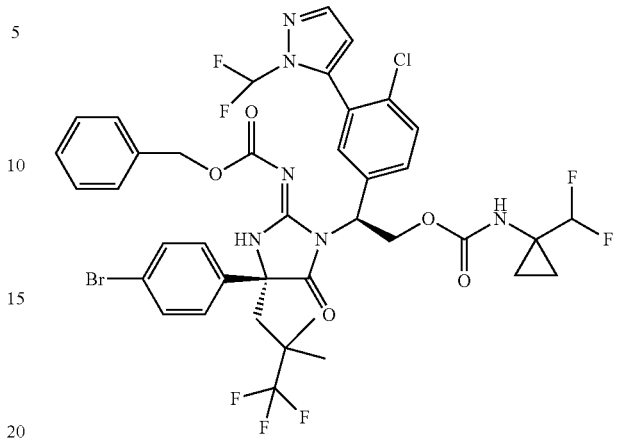

To a solution of isopropyl (R)-2-(3-((benzyloxy)carbonyl)thioureido)-2-(4-bromophenyl)-5,5,5-trifluoro-4,4-dimethylpentanoate (2.98 g, 5.0 mmol) and (S)-2-amino-2-(4-chloro-3-(1-(difluoromethyl)-1H-1,2,4-triazol-5-yl)phenyl)ethyl (1-(difluoromethyl)cyclopropyl)carbamate (6.0 mmol) in acetonitrile (20 mL) were sequentially added N-(3-dimethylaminopropyl)-N'-ethylcarbodiimide hydrochloride (10 mmol) and DIPEA (18 mmol). The reaction mixture was stirred at 50° C. for 16 hr. The mixture was then partitioned between EtOAc and brine. The organic layer was taken and concentrated. The residue was purified by silica gel column chromatography (0-100% EtOAc/hexanes) to afford the product. LCMS-ESI+(m/z): calc'd for $C_{38}H_{34}BrClF_7N_7O_5$: 916.1 [M+H]$^+$; found: 916.2 [M+H]$^+$.

Preparation of (S)-2-((R)-2-(((benzyloxy)carbonyl)imino)-5-oxo-4-(4-(4,4,5,5-tetramethyl-1,3,2-dioxaborolan-2-yl)phenyl)-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate

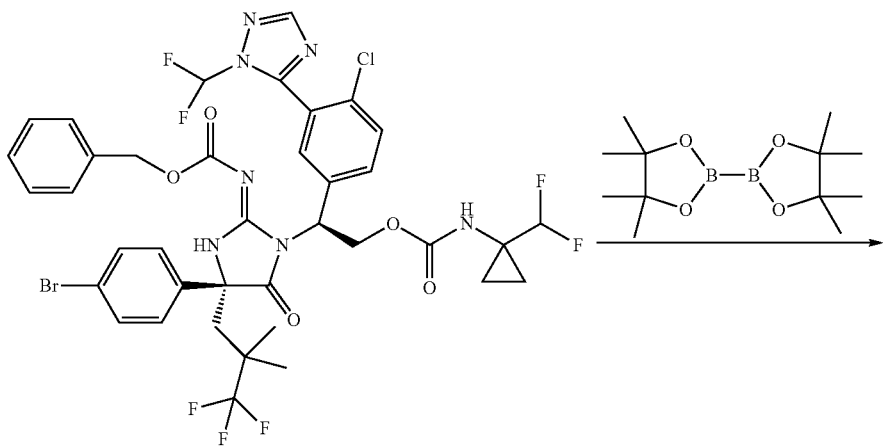

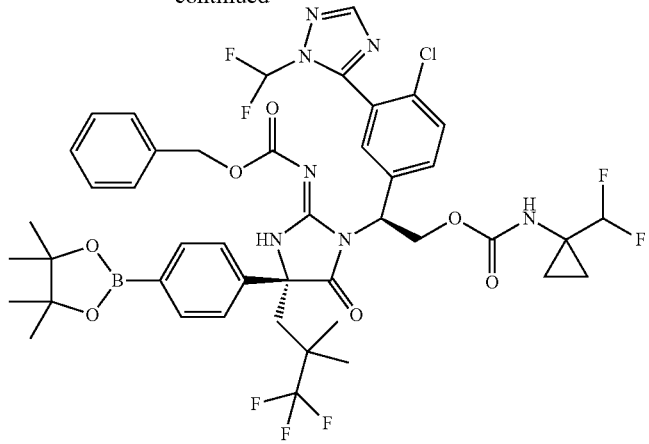

To a solution of (S)-2-((R)-2-(((benzyloxy)carbonyl)imino)-4-(4-bromophenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate (1.5 g, 1.64 mmol) and 4,4,5,5-tetramethyl-2-(4,4,5,5-tetramethyl-1,3,2-dioxaborolan-2-yl)-1,3,2-dioxaborolane (500 mg, 1.96 mmol) in dioxane (10 mL) were added [bis(diphenylphosphino)ferrocene]dichloropalladium(II) (0.16 mmol) and potassium acetate (7.36 mmol), and then purged with argon. The mixture was stirred at 95° C. for 2 hr. After cooling, the mixture was filtered through Celite, and the filtrate was concentrated. The residue was purified by silica gel column chromatography (ethyl acetate/hexanes) to afford the product. LCMS-ESI+(m/z): calc'd for $C_{44}H_{46}BClF_7N_7O_7$: 964.3 $[M+H]^+$; found: 964.1 $[M+H]^+$.

Example 1: Preparation of Compound 1

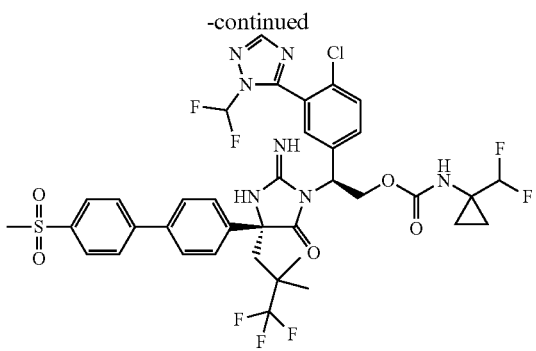

Compound 1

Preparation of (S)-2-((R)-2-(((benzyloxy)carbonyl)imino)-4-(4'-(methylsulfonyl)-[1,1'-biphenyl]-4-yl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate A mixture of (S)-2-((R)-2-(((benzyloxy)carbonyl)imino)-4-(4-bromophenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate (0.11 mmol), (4-methylsulfonylphenyl)boronic acid (110 mg, 0.55 mmol), Pd(PPh$_3$)$_4$ (0.022 mmol), K$_2$CO$_3$ (0.87 mmol), dioxane (2 mL) and water (0.2 mL) in a sealed vial was stirred at 85° C. for 2 hr. After cooling, the mixture was partitioned between ethyl acetate and water. The ethyl acetate layer was collected and concentrated. The residue was purified by silica gel column chromatography (0-100% gradient ethyl acetate/hexanes), affording the product.

Preparation of Compound 1, (S)-2-(4-chloro-3-(1-(difluoromethyl)-1H-1,2,4-triazol-5-yl)phenyl)-2-((R)-2-imino-4-(4'-(methylsulfonyl)-[1,1'-biphenyl]-4-yl)-5-oxo-4-(3,3,3-trifluoro-2,2-dimethylpropyl)imidazolidin-1-yl)ethyl (1-(difluoromethyl)cyclopropyl)carbamate To the product from the previous step, (S)-2-((R)-2-(((benzyloxy)carbonyl)imino)-4-(4'-(methylsulfonyl)-[1,1'- biphenyl]-4-yl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate was added trifluoroacetic acid (2 mL), and stirred at 45° C. for 16 hr. The resulting mixture was concentrated. The residue was purified by reverse phase HPLC (acetonitrile/water with 0.1% TFA) to give the product. LCMS-ESI+(m/z): calc'd for $C_{37}H_{36}ClF_7N_7O_5S$: 858.2 [M+H]$^+$; found: 858.1 [M+H]$^+$. $^1$H NMR (400 MHz, methanol-d$_4$) δ 8.15-7.16 (m, 13H), 6.00-5.60 (m, 2H), 5.21-5.09 (m, 1H), 4.72 (dd, J=11.7, 4.8 Hz, 1H), 3.20 (s, 3H), 2.81 (d, J=15.5 Hz, 1H), 2.52 (d, J=15.5 Hz, 1H), 1.22 (d, J=6.7 Hz, 6H), 1.14-1.01 (m, 2H), 1.00-0.86 (m, 2H).

Example 2: Preparation of Compound 2

Compound 2

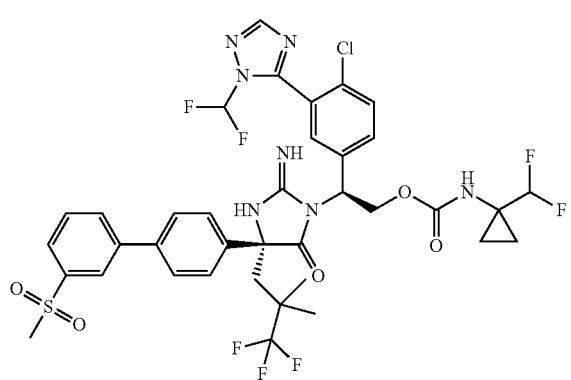

Compound 2 was prepared in a similar manner to prepare Compound 1, except that (3-methylsulfonylphenyl)boronic acid was used instead of (4-methylsulfonylphenyl)boronic acid. LCMS-ESI+(m/z): calc'd for $C_{37}H_{36}ClF_7N_7O_5S$: 858.2 [M+H]$^+$; found: 858.2 [M+H]$^+$. $^1$H NMR (400 MHz, methanol-d$_4$) δ 8.21 (t, J=1.8 Hz, 1H), 8.09-7.95 (m, 3H), 7.83-7.70 (m, 3H), 7.68-7.56 (m, 4H), 7.54-7.02 (m, 2H), 6.01-5.56 (m, 2H), 5.14 (dd, J=11.6, 9.7 Hz, 1H), 4.73 (dd, J=11.6, 4.8 Hz, 1H), 3.24 (s, 3H), 2.81 (d, J=15.5 Hz, 1H), 2.52 (d, J=15.5 Hz, 1H), 1.23 (d, J=7.9 Hz, 6H), 1.10 (t, J=3.6 Hz, 2H), 0.97-0.77 (m, 2H).

Example 3: Preparation of Compound 3

Compound 3

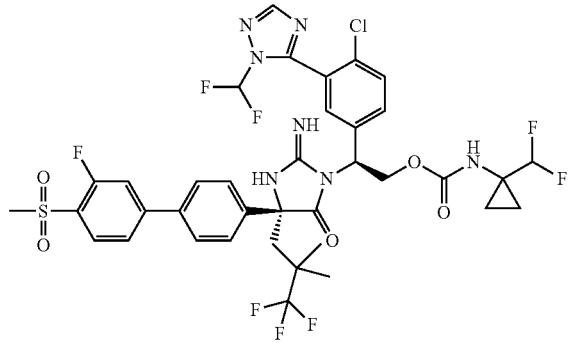

Compound 3 was prepared in a similar manner to prepare Compound 1, except that (3-fluoro-4-methylsulfonylphenyl)boronic acid was used instead of (4-methylsulfonylphenyl)boronic acid. LCMS-ESI+(m/z): calc'd for $C_{37}H_{36}ClF_8N_7O_5S$: 876.2 [M+H]$^+$; found: 876.2 [M+H]$^+$. $^1$H NMR (400 MHz, methanol-d$_4$) δ 8.19-7.95 (m, 2H), 7.87-7.68 (m, 4H), 7.61 (d, J=8.3 Hz, 4H), 7.54-7.17 (m, 2H), 6.00-5.59 (m, 2H), 5.15 (dd, J=11.6, 9.7 Hz, 1H), 4.72 (dd, J=11.7, 4.8 Hz, 1H), 3.33 (s, 3H), 2.80 (d, J=15.5 Hz, 1H), 2.51 (d, J=15.5 Hz, 1H), 1.22 (d, J=8.2 Hz, 6H), 1.15-1.00 (m, 2H), 1.01-0.85 (m, 2H).

Example 4: Preparation of Compound 4

Compound 4

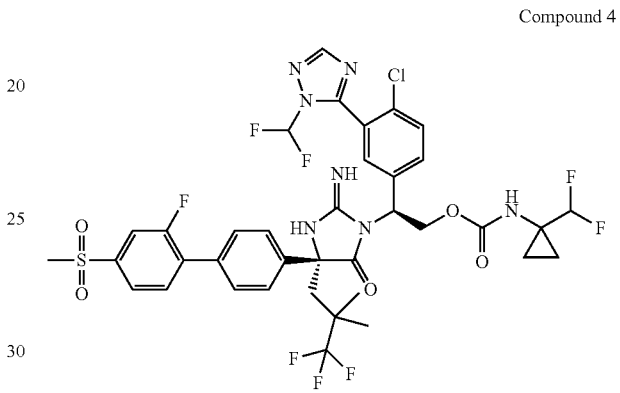

Compound 4 was prepared in a similar manner to prepare Compound 1, except that (2-fluoro-4-methylsulfonylphenyl)boronic acid was used instead of (4-methylsulfonylphenyl)boronic acid. LCMS-ESI+(m/z): calc'd for $C_{37}H_{36}ClF_8N_7O_5S$: 876.2 [M+H]$^+$; found: 876.2 [M+H]$^+$. $^1$H NMR (400 MHz, methanol-d$_4$) δ 8.14 (s, 1H), 8.04-7.16 (m, 11H), 6.00-5.59 (m, 2H), 5.16 (dd, J=11.6, 9.7 Hz, 1H), 4.72 (dd, J=11.7, 4.8 Hz, 1H), 3.23 (s, 3H), 2.81 (d, J=15.5 Hz, 1H), 2.52 (d, J=15.5 Hz, 1H), 1.22 (d, J=7.8 Hz, 6H), 1.16-1.01 (m, 2H), 1.00-0.85 (m, 2H).

Example 5: Preparation of Compound 5

Compound 5

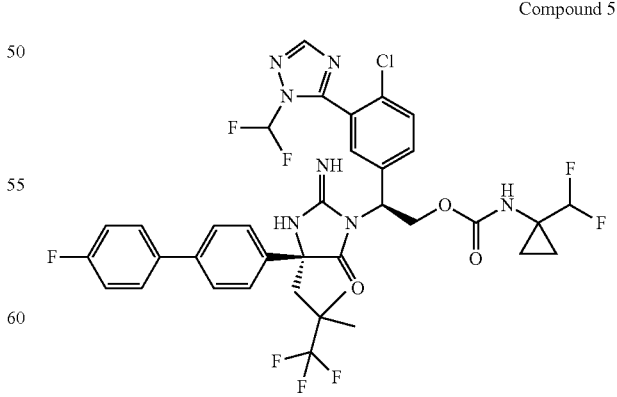

Compound 5 was prepared in a similar manner to prepare Compound 1, except that (4-fluorophenyl)boronic acid was used instead of (4-methylsulfonylphenyl)boronic acid.

LCMS-ESI+(m/z): calc'd for C₃₆H₃₃ClF₈N₇O₃: 798.2 [M+H]⁺; found: 798.1 [M+H]⁺. ¹H NMR (400 MHz, methanol-d₄) δ 8.02 (s, 1H), 7.98 (s, 1H), 7.75-7.10 (m, 11H), 5.98-5.58 (m, 2H), 5.21-5.09 (m, 1H), 4.72 (dd, J=11.6, 4.8 Hz, 1H), 2.80 (d, J=15.5 Hz, 1H), 2.50 (d, J=15.5 Hz, 1H), 1.22 (d, J=5.9 Hz, 6H), 1.12-1.00 (m, 2H), 0.99-0.87 (m, 2H).

Example 6: Preparation of Compound 6

Compound 6

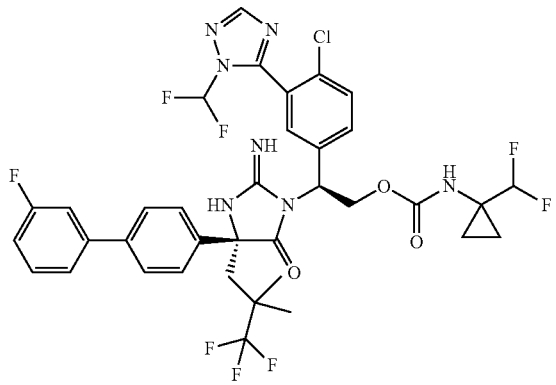

Compound 5 was prepared in a similar manner to prepare Compound 1, except that (3-fluorophenyl)boronic acid was used instead of (4-methylsulfonylphenyl)boronic acid. LCMS-ESI+(m/z): calc'd for C₃₆H₃₃ClF₈N₇O₃: 798.2 [M+H]⁺; found: 798.1 [M+H]⁺. ¹H NMR (400 MHz, methanol-d₄) δ 8.02 (s, 1H), 7.98 (s, 1H), 7.76-7.07 (m, 11H), 6.00-5.59 (m, 2H), 5.21-5.09 (m, 1H), 4.72 (dd, J=11.7, 4.8 Hz, 1H), 2.81 (d, J=15.5 Hz, 1H), 2.51 (d, J=15.5 Hz, 1H), 1.22 (d, J=4.7 Hz, 6H), 1.13-0.99 (m, 2H), 0.99-0.84 (m, 2H).

Example 7: Preparation of Compound 7

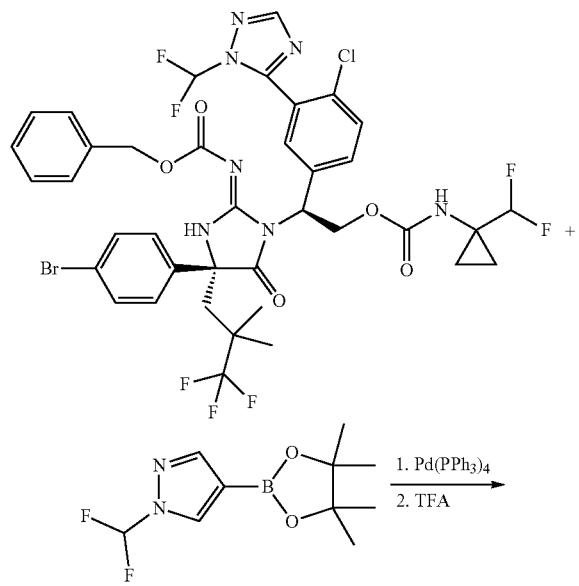

Compound 7

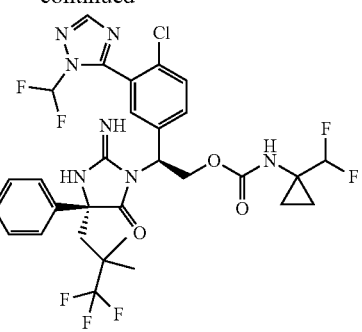

Preparation of (S)-2-((R)-2-(((benzyloxy)carbonyl)imino)-4-(4-(1-(difluoromethyl)-1H-pyrazol-4-yl)phenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate A mixture of (S)-2-((R)-2-(((benzyloxy)carbonyl)imino)-4-(4-bromophenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate (0.11 mmol), 1-(difluoromethyl)-4-(4,4,5,5-tetramethyl-1,3,2-dioxaborolan-2-yl)pyrazole (0.55 mmol), Pd(PPh₃)₄ (0.022 mmol), K₂CO₃ (0.87 mmol), dioxane (2 mL) and water (0.2 mL) in a sealed vial was stirred at 88° C. for 1.5 hr. After cooling, the mixture was partitioned between ethyl acetate and water. The ethyl acetate layer was collected and concentrated. The residue was purified by silica gel column chromatography (0-100% gradient ethyl acetate/hexanes), affording the product.

Preparation of Compound 7, (S)-2-(4-chloro-3-(1-(difluoromethyl)-1H-1,2,4-triazol-5-yl)phenyl)-2-((R)-2-imino-4-(4'-(methylsulfonyl)-[1,1'-biphenyl]-4-yl)-5-oxo-4-(3,3,3-trifluoro-2,2-dimethylpropyl)imidazolidin-1-yl)ethyl (1-(difluoromethyl)cyclopropyl)carbamate To the product from the previous step, (S)-2-((R)-2-(((benzyloxy)carbonyl)imino)-4-(4-(1-(difluoromethyl)-1H-pyrazol-4-yl)phenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate was added trifluoroacetic acid (2 mL), and stirred at 45° C. for 16 hr. The resulting mixture was concentrated. The residue was purified by reverse phase HPLC (acetonitrile/water with 0.1% TFA) to give the product (44 mg, 43% in two steps). LCMS-ESI+(m/z): calc'd for C₃₄H₃₂ClF₉N₉O₃: 820.2 [M+H]⁺; found: 820.1 [M+H]⁺. ¹H NMR (400 MHz, methanol-d₄) δ 8.51 (s, 1H), 8.14 (s, 1H), 8.07 (s, 1H), 7.95 (s, 1H), 7.78-7.08 (m, 8H), 5.99-5.58 (m, 2H), 5.19-5.04 (m, 1H), 4.72 (dd, J=11.6, 4.9 Hz, 1H), 2.78 (d, J=15.5 Hz, 1H), 2.48 (d, J=15.5 Hz, 1H), 1.21 (d, J=5.8 Hz, 6H), 1.14-1.04 (m, 2H), 0.99-0.87 (m, 2H).

Example 8: Preparation of Compound 8

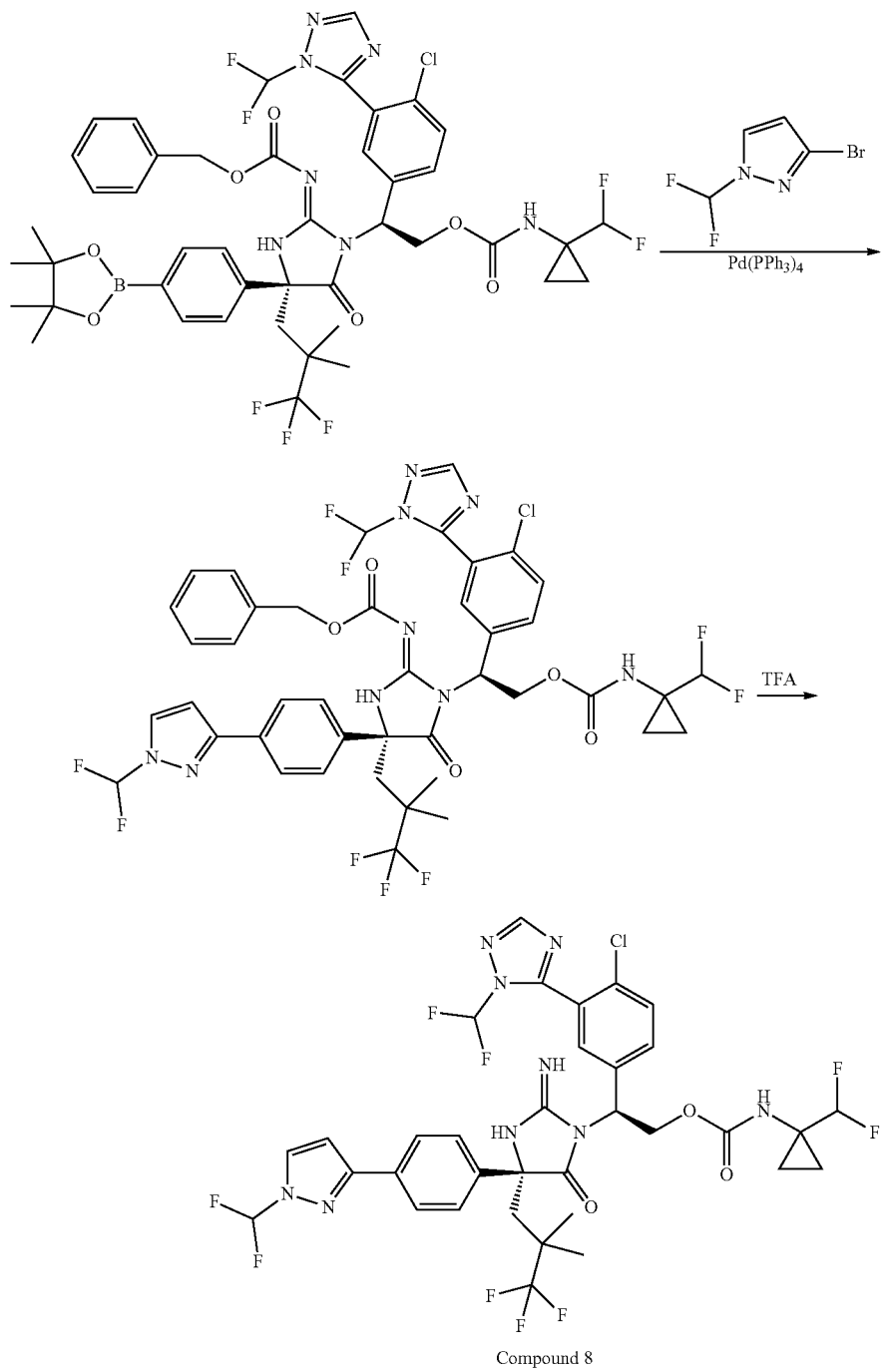

Compound 8

Preparation of (S)-2-((R)-2-(((benzyloxy)carbonyl)imino)-4-(4-(1-(difluoromethyl)-1H-pyrazol-3-yl)phenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate A mixture of (S)-2-((R)-2-(((benzyloxy)carbonyl)imino)-5-oxo-4-(4-(4,4,5,5-tetramethyl-1,3,2-dioxaborolan-2-yl)phenyl)-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate (0.042 mmol), 3-bromo-1-(difluoromethyl)pyrazole (0.33 mmol), Pd(PPh$_3$)4 (0.0083 mmol), potassium carbonate (0.10 mmol), dioxane (1 mL) and water (0.1 mL) in a sealed vial was stirred at 90° C. for 1 hr. After cooling, the mixture was partitioned between ethyl acetate and water. The ethyl acetate layer was concentrated. The residue was purified by silica gel column chromatography (0-100% gradient EtOAc/hexanes) to afford the product (12 mg, 30%).

Preparation of Compound 8, (S)-2-(4-chloro-3-(1-(difluoromethyl)-1H-1,2,4-triazol-5-yl)phenyl)-2-((R)-4-(4-(1-(difluoromethyl)-1H-pyrazol-3-yl)phenyl)-2-imino-5-oxo-4-(3,3,3-trifluoro-2,2-dimethylpropyl)imidazolidin-1-yl)ethyl (1-(difluoromethyl)cyclopropyl)carbamate To the product from the previous step, (S)-2-((R)-2-(((benzyloxy)carbonyl)imino)-4-(4-(1-(difluoromethyl)-1H-pyrazol-3-yl)phenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate (0.0126 mmol) was added trifluoroacetic acid (2 mL), and stirred at 45° C. for 16 hr. The resulting mixture was concentrated. The residue was purified by reverse phase HPLC (acetonitrile/water with 0.1% TFA) to give the product (5.9 mg, 50%). LCMS-ESI+ (m/z): calc'd for $C_{34}H_{32}ClF_9N_9O_3$: 820.2 [M+H]$^+$; found: 820.1 [M+H]$^+$. $^1$H NMR (400 MHz, methanol-$d_4$) δ 8.15 (d, J=2.7 Hz, 1H), 8.06-7.08 (m, 10H), 6.95 (d, J=2.8 Hz, 1H), 6.01-5.58 (m, 2H), 5.18-5.05 (m, 1H), 4.72 (dd, J=11.7, 4.8 Hz, 1H), 2.81 (d, J=15.5 Hz, 1H), 2.50 (d, J=15.5 Hz, 1H), 1.22 (d, J=3.4 Hz, 6H), 1.14-1.00 (m, 2H), 0.99-0.86 (m, 2H).

Example 9: Preparation of Compound 9

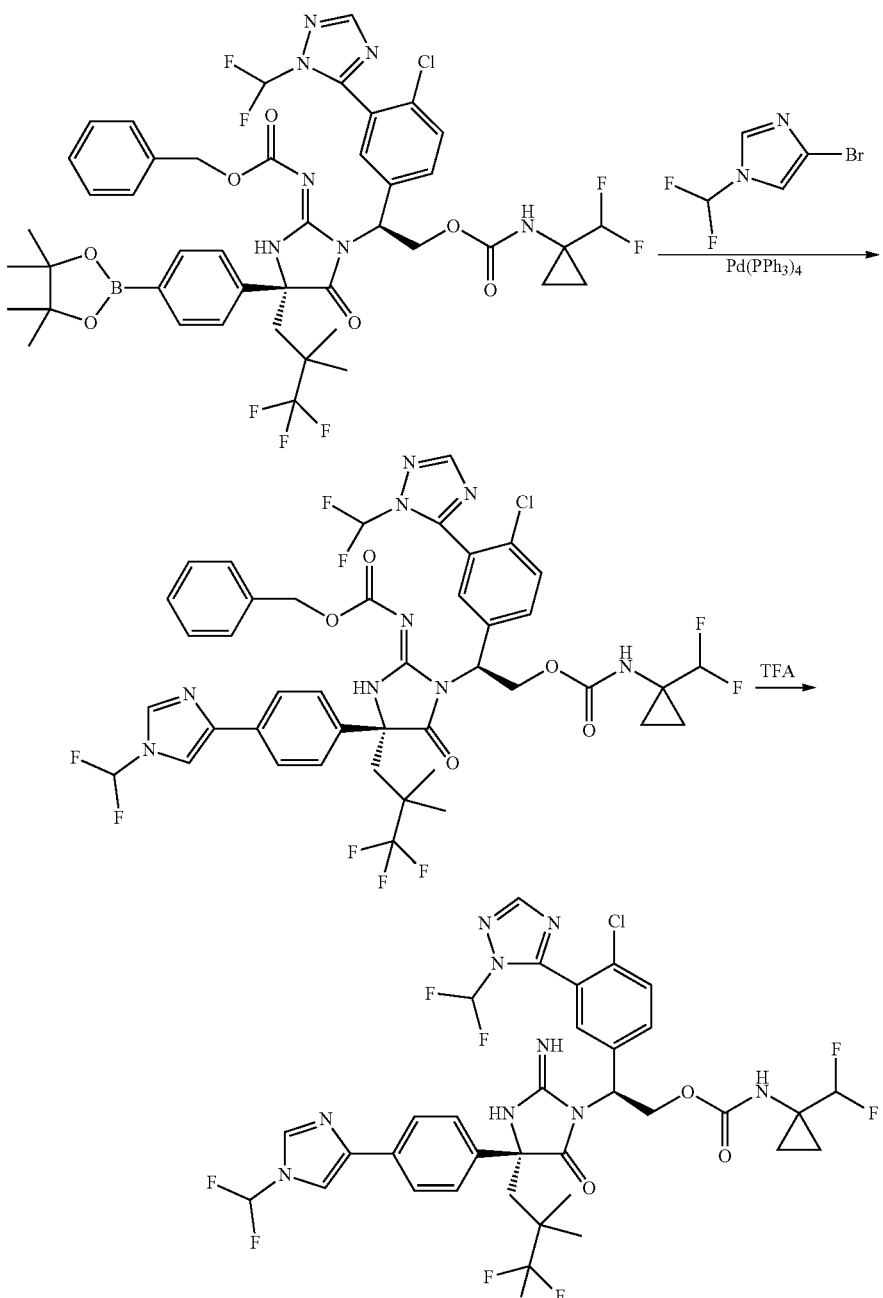

Compound 9

Compound 9, (S)-2-(4-chloro-3-(1-(difluoromethyl)-1H-1,2,4-triazol-5-yl)phenyl)-2-((R)-4-(4-(1-(difluoromethyl)-1H-imidazol-4-yl)phenyl)-2-imino-5-oxo-4-(3,3,3-trifluoro-2,2-dimethylpropyl)imidazolidin-1-yl)ethyl (1-(difluoromethyl)cyclopropyl)carbamate, was prepared in a similar manner to prepare Compound 8, except that 4-bromo-1-(difluoromethyl)-1H-imidazole is used instead of 3-bromo-1-(difluoromethyl)pyrazole. LCMS-ESI+(m/z): calc'd for $C_{34}H_{32}ClF_9N_9O_3$: 820.2 [M+H]$^+$; found: 820.2 [M+H]$^+$. $^1$H NMR (400 MHz, methanol-$d_4$) δ 8.21 (s, 1H), 8.03 (s, 1H), 7.95 (d, J=1.3 Hz, 1H), 7.91 (s, 1H), 7.78-7.08 (m, 8H), 5.95-5.59 (m, 2H), 5.10 (t, 1H), 4.70 (dd, J=11.7, 4.9 Hz, 1H), 2.76 (d, J=15.6 Hz, 1H), 2.47 (d, J=15.5 Hz, 1H), 1.19 (d, J=5.8 Hz, 6H), 1.07 (m, 2H), 0.92 (m, 2H).

Biological Assays

MT-4 HIV Assay.

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Agilent ECHO acoustic dispenser. Each plate contained up to 8 test compounds, with negative (No Drug Control) and 5 uM AZT positive controls. MT-4 cells were pre-infected with 10 uL of either RPMI (mock-infected) or a fresh 1:250 dilution of an HIV-1 (IIIB) concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates to quantify the amount of luciferase. EC$_{50}$ and CC$_{50}$ values were defined as the compound concentration that causes a 50% decrease in luminescence signal, and were calculated using a sigmoidal dose-response model to generate curve fits. Data for certain compounds are reported in Table 1 below.

TABLE 1

| COMPD # | STRUCTURE | HIV PI IC$_{50}$ (nM) | MT4 EC$_{50}$ (nM) |
| --- | --- | --- | --- |
| 1 | 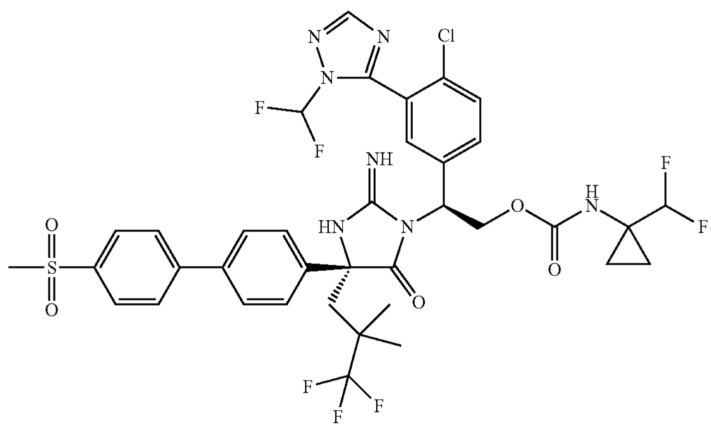 [SMILES: CC(C)(C[C@]1(c2ccc(-c3ccc(S(C)(=O)=O)cc3)cc2)NC(=N)N([C@H](COC(=O)NC2(C(F)F)CC2)c2ccc(Cl)c(-c3ncnn3C(F)F)c2)C1=O)C(F)(F)F] | 1.8 | 13.2 |
| 2 | 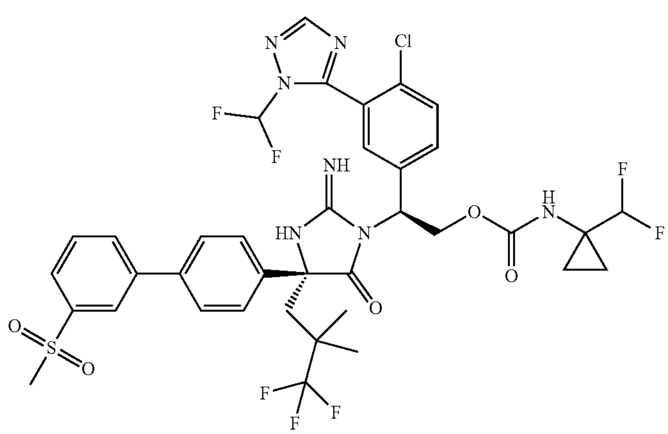 [SMILES: CC(C)(C[C@]1(c2ccc(-c3cccc(S(C)(=O)=O)c3)cc2)NC(=N)N([C@H](COC(=O)NC2(C(F)F)CC2)c2ccc(Cl)c(-c3ncnn3C(F)F)c2)C1=O)C(F)(F)F] | 2.9 | 27.5 |

TABLE 1-continued
| COMPD # | STRUCTURE | HIV PI IC$_{50}$ (nM) | MT4 EC$_{50}$ (nM) |
|---|---|---|---|
| 3 | 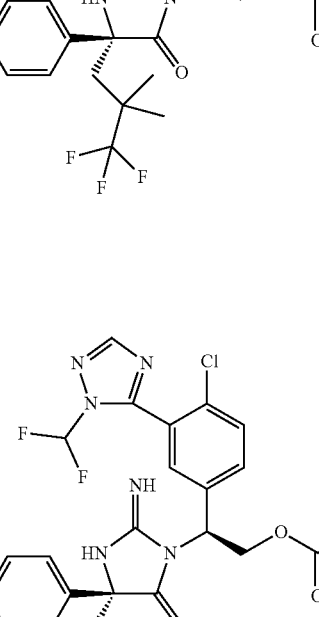 | 2.9 | 11.1 |
| 4 | 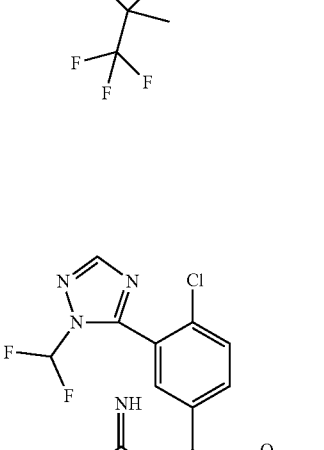 | 2.4 | 11.3 |
| 5 | 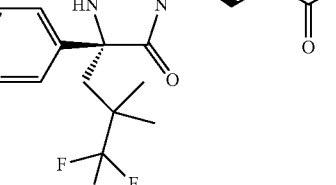 | 4.5 | 63.1 |

TABLE 1-continued

| COMPD # | STRUCTURE | HIV PI IC$_{50}$ (nM) | MT4 EC$_{50}$ (nM) |
|---|---|---|---|
| 6 | 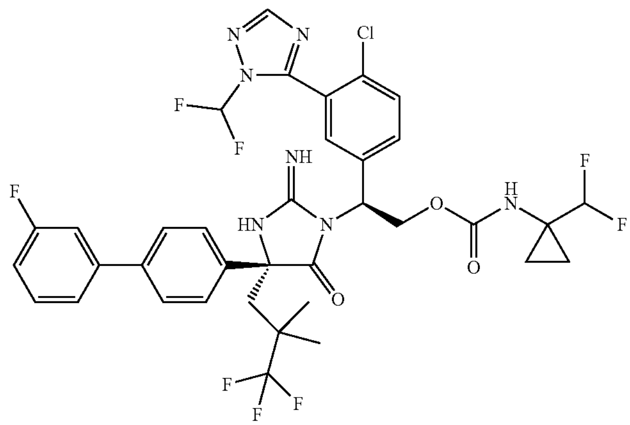 [SMILES: CC(C)(C[C@]1(c2ccc(-c3cccc(F)c3)cc2)NC(=N)N([C@H](COC(=O)NC2(C(F)F)CC2)c2ccc(Cl)c(-c3ncnn3C(F)F)c2)C1=O)C(F)(F)F] | 2.3 | 50.0 |
| 7 | 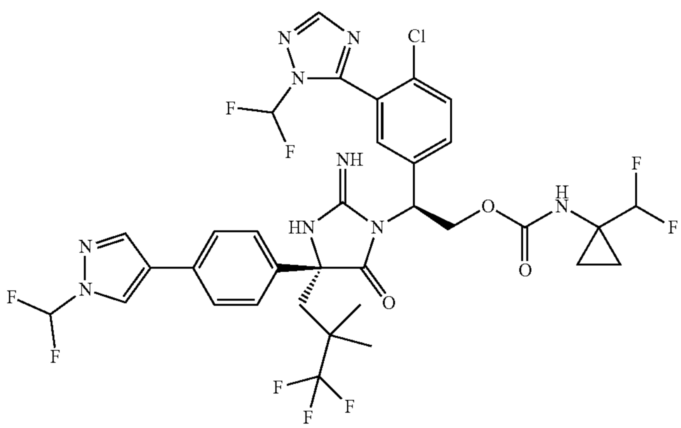 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] | 1.8 | 7.8 |
| 8 | 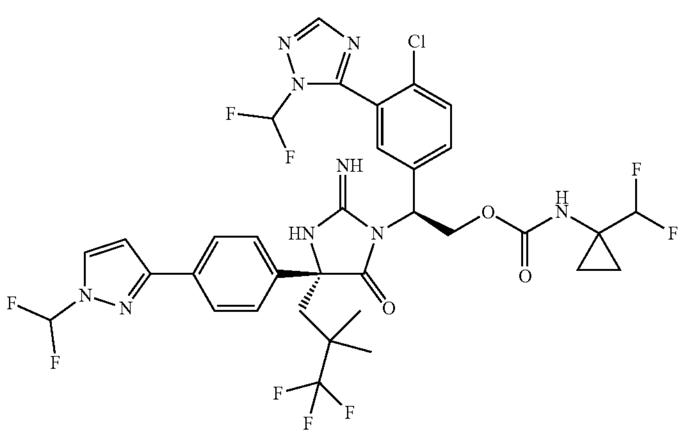 [SMILES: CC(C)(C[C@]1(c2ccc(-c3ccn(C(F)F)n3)cc2)NC(=N)N([C@H](COC(=O)NC2(C(F)F)CC2)c2ccc(Cl)c(-c3ncnn3C(F)F)c2)C1=O)C(F)(F)F] | 2.0 | 8.4 |

TABLE 1-continued

| COMPD # | STRUCTURE | HIV PI IC$_{50}$ (nM) | MT4 EC$_{50}$ (nM) |
|---|---|---|---|
| 9 | 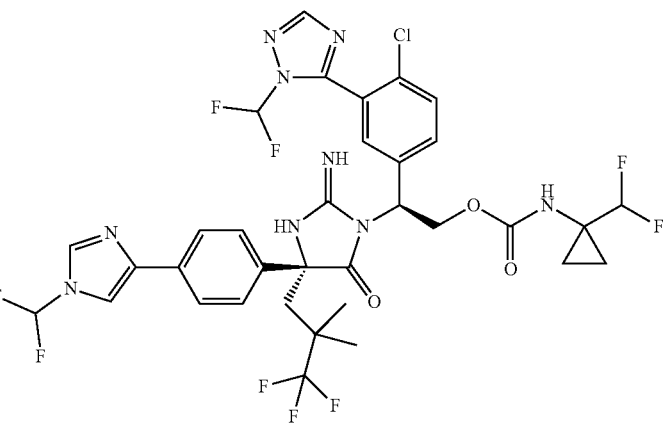 | 5.7 | 26.3 |

MT-4 HIV High Resolution Antiviral Assay

Assay protocol is identical to that described for the MT-4 antiviral assay with the following changes: Each drug was run in 2 series of quadruplicates with different starting concentrations for each series and 19 1.5 fold dilutions performed across the plate. This resulted in an inhibition curve with 40 data points for each compound. Data were analyzed and Hill coefficients determined in Graph Pad Prism (San Diego, Calif.). EC$_{95}$s were determined by the formula EC$_{95}$=(19)$^{1/hill\ coefficient \times EC_{50}}$. EC$_{95}$ for Examples 1 and 7 were 24.9 and 17.8 nM, respectively.

Liver Microsomal Stability Protocol

Test compounds and one control compound (verapamil) were tested in 3 different species in duplicate sets.

General Conditions:

Test compound concentration: 1 µM; Protein concentration: 0.5 mg/mL (for dog, rat, and human liver microsomes); Cofactor: NADPH-Regenerating system (NRS) solution.
Time-points: 2, 12, 25, 45, and 65 minutes.
Reaction composition (in each incubation well) contains:

| | |
|---|---|
| 5 µL compound (50 uM stock solution, 50:50 ACN:H$_2$O) | |
| 25 µL NRS solution | |
| 6.25 µL 20 mg/mL liver microsomes | |
| 213.75 µL 100 mM KPO4, pH 7.4 | |
| 250 µL total volume | |

At an incubation temperature of 37° C., the reaction was started with addition of NADPH Regeneration System, at each time point, 25 µL of the reaction mixture was removed and added to a plate with 225 µL quenching solution (50% MeOH, 25 ACN, 25% H$_2$O, and 200 nM labetalol as internal standard). After plates were vortexed, they were centrifuged for 30 minutes to remove proteins. About 100 µL supernatant was removed to a new plate and diluted with 150 µL water. About 20 µL of the mixture was injected into LC/MS/MS system to monitor the compound's response. In vitro measured t$_{1/2}$ was used to calculate Cl$_{int}$ values.

Half-lives of atazanavir and darunavir measured in this assay using human liver microsomes were 26-107 min and 16-32 min, respectively. In contrast, half-lives of all Compounds 1-9 were ≥395 min. Such high metabolic stability offers the potential for less frequent dosing without a booster.

HIV Protease Enzyme Inhibition (PI) Activity

Inhibitor potency against HIV protease can be measured using an enzymatic assay with a fluorogenic readout. To a reaction buffer containing 100 mM ammonium acetate at pH 5.3, 100 mM NaCl, 1 mM EDTA, 1 mM DTT, 0.25 mg/mL BSA and 1% DMSO are added 10 nM of recombinant HIV protease (concentration based on protein monomer) and test compound at one of various concentrations. After a 10-minute pre-incubation, the enzymatic reaction is initiated by the addition of the fluorogenic substrate (2-aminobenzoyl)Thr-Ile-Nle-(p-nitro)Phe-Gln-Arg (Bachem; Product No. H-2992) (SEQ ID NO: 1) to a final concentration of 40 µM. The total volume of the assay solution is 100 µL. The reaction is measured over 10 minutes on a Tecan Infinite M1000 plate reader using an excitation wavelength of 320 nm and a detection wavelength of 420 nm. The slopes of the progress curves are the measure of reaction rates. Reaction rates are plotted as a function of inhibitor concentration, and the data are fit with a four-parameter logistic fit using Graphpad PRISM software to yield IC$_{50}$ values.

Resistance Profiling

Resistance testing was done by Monogram Biosciences using their proprietary PhenoSense HIV assay. This assay evaluates drug susceptibility by using a single replication cycle recombinant virus containing the protease (amino acids 1-99 plus p7/p1/p6 gag cleavage sites) and reverse transcriptase (amino acids 1-304) coding regions of HIV-1 from a patient blood sample. The data for Compound 7 compared with atazanavir and darunavir are shown in Table 2 below. The mean fold change in susceptibility for Example 7 was 2.4, while those for atazanavir and darunavir were 17.7 and 9.3, respectively.

TABLE 2

| | Fold Change in $EC_{50}$ | | |
|---|---|---|---|
| Resistance Mutations | Atazanavir | Darunavir | Example 7 |
| D30N L33F N88D L90M | 4.68 | 0.88 | 3.62 |
| L10F/L D30N L33F I54L N88D L90M | 15 | 4.55 | 2.57 |
| L10F/L D30N I54V N88D L90M | 29 | 1.96 | 5.32 |
| M46I L76V I84V | 1.36 | 4.28 | 2.04 |
| L10F M46I I47V I50V I54V G73S I84V L90M | 19 | >504 | 3.51 |
| L10I M46L I54V V82A | 9.73 | 0.9 | 5.84 |
| L10I L33F/L G48V G73S V82A | >91 | 1.98 | 2.34 |
| L10I V32I L33F M46I I54L L89V | 89 | >504 | 0.82 |
| L10I L33F M46L G48V I54M V82A I84V L90M | 70 | 19 | 2.9 |
| L10V L33F M46I I54V V82A I84V L90M/L | 9.69 | 6.05 | 2.6 |
| L10I M46L I54V V82F L90M | 24 | 2.07 | 4.33 |
| L10F M46L I54V V82A I84V | 73 | 6 | 0.91 |
| L10I M46I G48V I50V V82A L90M | 39 | 11 | 9.22 |
| L10I V32I M46I I47V I50V I54L L90M | 25 | >504 | 3.92 |
| L10I L33F M46I I54V V82A I84V | 44 | 22 | 2.49 |
| L10I V32I M46I I47V G48V I54M V82T L90M | 9.49 | 5.84 | 2.84 |
| L10V/L M46I I50L V82A | 69 | 1.68 | 4.77 |
| L10I L33F G48V I50L I54V/I V82A | 70 | 1.19 | 0.72 |
| L10I I50 V82A L90M | 33 | 0.63 | 1.7 |
| L10V L33F I50L L90M | >91 | 1.15 | 3.09 |
| L10I M46I I50V | 2.39 | 15 | 2.2 |
| L10F V32I M46I I47V I50V I54L I84V | 5.44 | >504 | 1.08 |
| L33F M46I I50V L76V | 1.84 | 45 | 1.39 |
| L10F L33F M46I I50V V82A N88D L89V | 1.25 | 24 | 0.58 |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound selected from one of:

| Compound # | Structure |
| --- | --- |
| 1 | 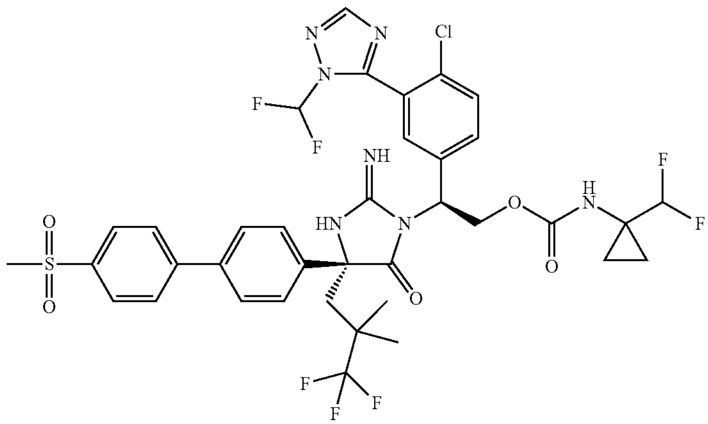 [SMILES: CC(C)(C[C@]1(c2ccc(-c3ccc(S(C)(=O)=O)cc3)cc2)NC(=N)N([C@H](COC(=O)NC2(C(F)F)CC2)c2ccc(Cl)c(-c3ncnn3C(F)F)c2)C1=O)C(F)(F)F] |
| 2 | 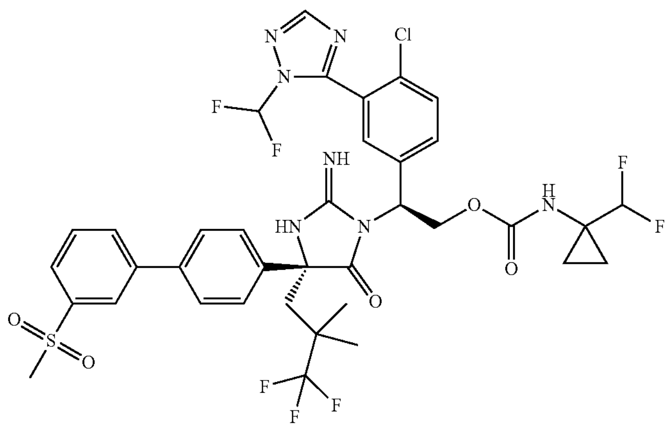 [SMILES: CC(C)(C[C@]1(c2ccc(-c3cccc(S(C)(=O)=O)c3)cc2)NC(=N)N([C@H](COC(=O)NC2(C(F)F)CC2)c2ccc(Cl)c(-c3ncnn3C(F)F)c2)C1=O)C(F)(F)F] |
| 3 | 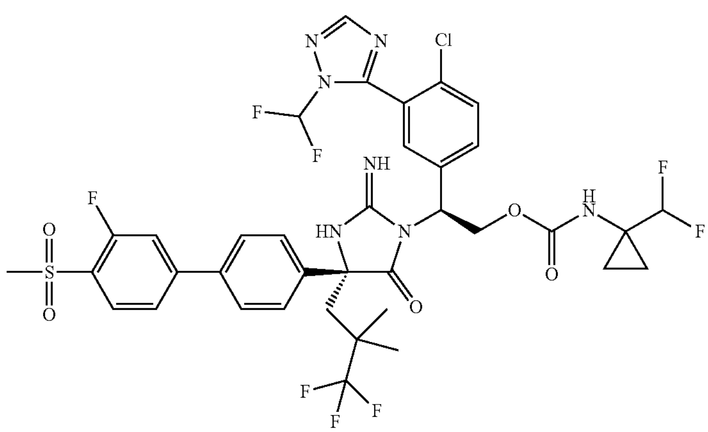 |

| Compound # | Structure |
|---|---|
| 4 | 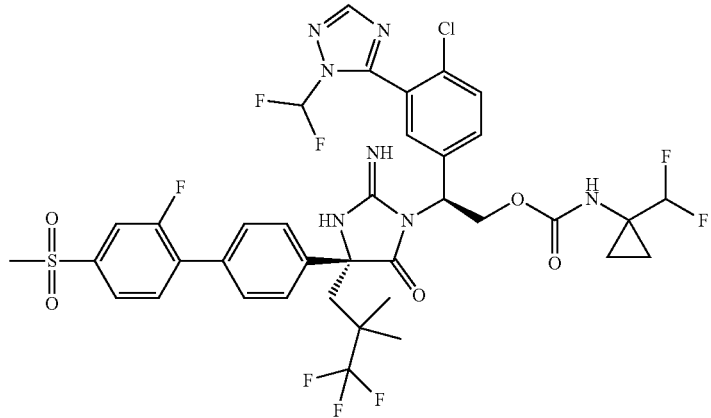 [SMILES: CC(C)(C[C@]1(c2ccc(-c3ccc(S(C)(=O)=O)cc3F)cc2)NC(=N)N([C@H](COC(=O)NC2(C(F)F)CC2)c2ccc(Cl)c(-c3ncnn3C(F)F)c2)C1=O)C(F)(F)F] |
| 5 | 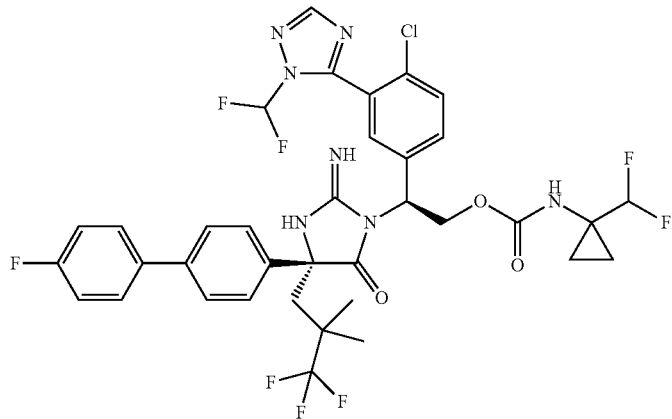 [SMILES: CC(C)(C[C@]1(c2ccc(-c3ccc(F)cc3)cc2)NC(=N)N([C@H](COC(=O)NC2(C(F)F)CC2)c2ccc(Cl)c(-c3ncnn3C(F)F)c2)C1=O)C(F)(F)F] |
| 6 | 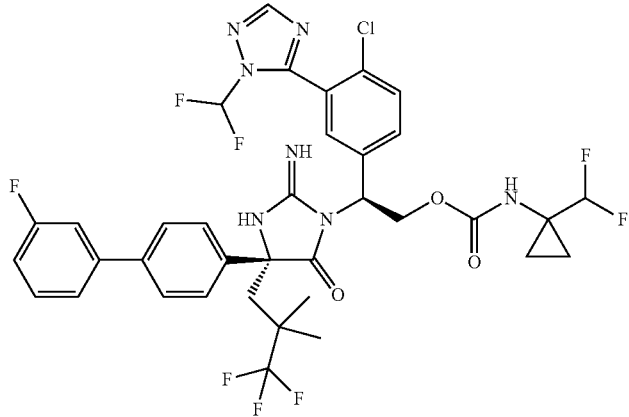 [SMILES: CC(C)(C[C@]1(c2ccc(-c3cccc(F)c3)cc2)NC(=N)N([C@H](COC(=O)NC2(C(F)F)CC2)c2ccc(Cl)c(-c3ncnn3C(F)F)c2)C1=O)C(F)(F)F] |

| Compound # | Structure |
|---|---|
| 7 | 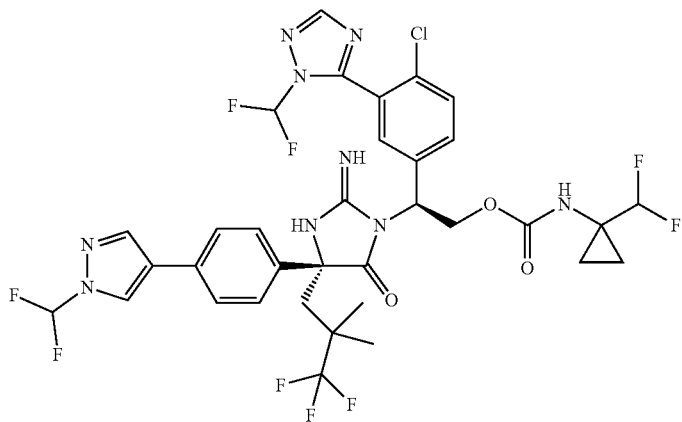 [SMILES: CC(C)(C[C@]1(c2ccc(-c3cnn(C(F)F)c3)cc2)NC(=N)N([C@H](COC(=O)NC2(C(F)F)CC2)c2ccc(Cl)c(-c3ncnn3C(F)F)c2)C1=O)C(F)(F)F] |
| 8 | 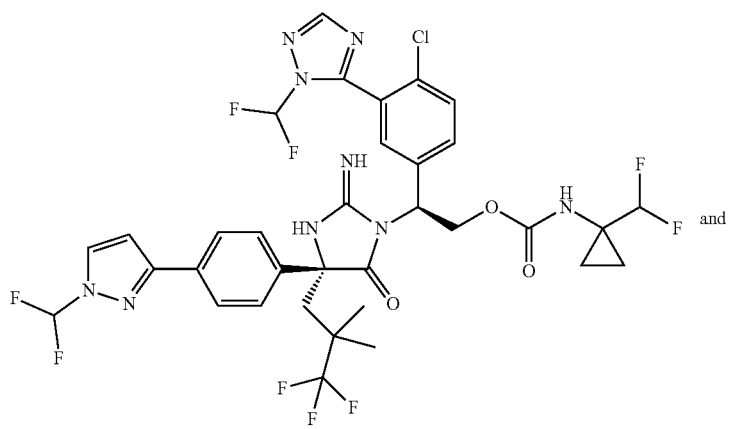 [SMILES: CC(C)(C[C@]1(c2ccc(-c3ccn(C(F)F)n3)cc2)NC(=N)N([C@H](COC(=O)NC2(C(F)F)CC2)c2ccc(Cl)c(-c3ncnn3C(F)F)c2)C1=O)C(F)(F)F] and |
| 9 | 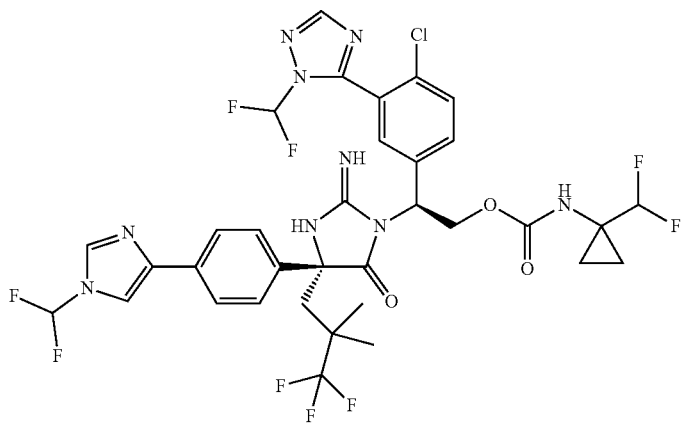 [SMILES: CC(C)(C[C@]1(c2ccc(-c3cn(C(F)F)cn3)cc2)NC(=N)N([C@H](COC(=O)NC2(C(F)F)CC2)c2ccc(Cl)c(-c3ncnn3C(F)F)c2)C1=O)C(F)(F)F] |
or a pharmaceutically acceptable salt thereof.

2. The compound of claim 1, wherein the compound is Compound 1 having the structure:

(Compound 1)

or a pharmaceutically acceptable salt thereof.

3. The compound of claim 1, wherein the compound is Compound 2 having the structure:

(Compound 2)

or a pharmaceutically acceptable salt thereof.

4. The compound of claim 1, wherein the compound is Compound 3 having the structure:

(Compound 3)

or a pharmaceutically acceptable salt thereof.

5. The compound of claim 1, wherein the compound is Compound 4 having the structure:

(Compound 4)

or a pharmaceutically acceptable salt thereof.

6. The compound of claim 1, wherein the compound is Compound 5 having the structure:

(Compound 5)

or a pharmaceutically acceptable salt thereof.

7. The compound of claim 1, wherein the compound is Compound 6 having the structure:

(Compound 6)

or a pharmaceutically acceptable salt thereof.

8. The compound of claim 1, wherein the compound is Compound 7 having the structure:

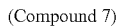

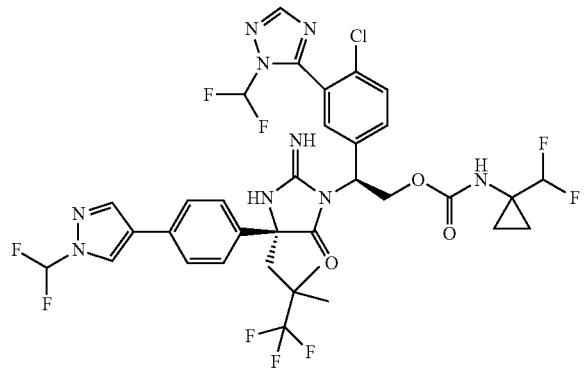

or a pharmaceutically acceptable salt thereof.

9. The compound of claim 1, wherein the compound is Compound 8 having the structure:

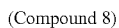

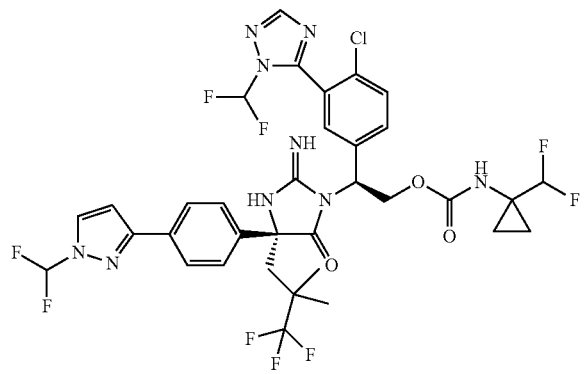

or a pharmaceutically acceptable salt thereof.

10. The compound of claim 1, wherein the compound is Compound 9 having the structure:

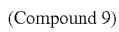

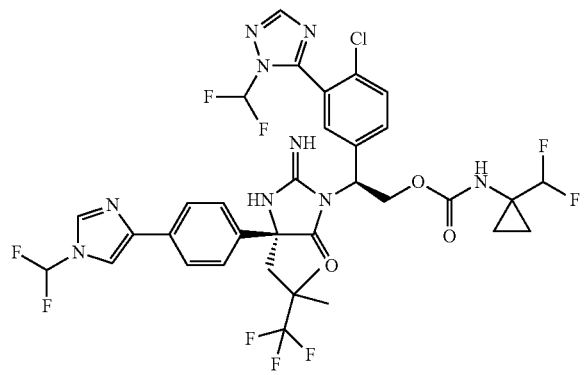

or a pharmaceutically acceptable salt thereof.

11. A pharmaceutical composition comprising the compound of claim 1, and at least one pharmaceutically acceptable excipient.

12. The pharmaceutical composition of claim 11, further comprising one or more additional therapeutic agents.

13. A method of treating a human immunodeficiency virus (HIV) infection comprising administering a therapeutically effective amount of the compound of claim 1, to a subject in need thereof.

14. The method of claim 13, wherein the method comprises administering the compound of claim 1, in combination with one, two, three, or four additional therapeutic agents.

15. The method of claim 14, wherein the additional therapeutic agents are selected from the group consisting of combination drugs for HIV, other drugs for treating HIV, HIV protease inhibitors, non-nucleoside or non-nucleotide inhibitors of HIV reverse transcriptase, nucleoside or nucleotide inhibitors of HIV reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors, cell therapies, latency reversing agents, compounds that target the HIV capsid, immune-based therapies, phosphatidylinositol 3-kinase (PI3K) inhibitors, HIV antibodies, bispecific antibodies, therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, long acting HIV regimens, and contraceptives, or any combinations of distinct agents thereof.

16. The method of claim 14, wherein the additional therapeutic agents are selected from the group consisting of HIV protease inhibiting compounds, non-nucleoside inhibitors of HIV reverse transcriptase, non-nucleotide inhibitors of HIV reverse transcriptase, nucleoside inhibitors of HIV reverse transcriptase, nucleotide inhibitors of HIV reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations of distinct agents thereof.

17. The method of claim 14, wherein the additional therapeutic agents are selected from the group consisting of 4'-ethynyl-2-fluoro-2'-deoxyadenosine, bictegravir or a pharmaceutically acceptable salt thereof, abacavir sulfate, tenofovir, tenofovir disoproxil, tenofovir disoproxil fumarate, tenofovir disoproxil hemifumarate, tenofovir alafenamide, and tenofovir alafenamide hemifumarate.

18. The method of claim 14, wherein the additional therapeutic agents are selected from the group consisting of 4'-ethynyl-2-fluoro-2'-deoxyadenosine, bictegravir or a pharmaceutically acceptable salt thereof, tenofovir alafenamide, tenofovir alafenamide fumarate and tenofovir alafenamide hemifumarate.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: synthetic polypeptide substrate
<220> FEATURE:
<221> NAME/KEY: MOD_RES
<222> LOCATION: (1)..(1)
<223> OTHER INFORMATION: 2-aminobenzoyl
<220> FEATURE:
<221> NAME/KEY: misc_feature
<222> LOCATION: (3)..(3)
<223> OTHER INFORMATION: Xaa = norleucine (Nle)
<220> FEATURE:
<221> NAME/KEY: MOD_RES
<222> LOCATION: (4)..(4)
<223> OTHER INFORMATION: p-nitro

<400> SEQUENCE: 1

Thr Ile Xaa Phe Gln Arg
1               5